(12) United States Patent
Ning et al.

(10) Patent No.: US 8,792,965 B2
(45) Date of Patent: Jul. 29, 2014

(54) METHODS AND APPARATUS OF CONE BEAM CT IMAGING AND IMAGE-GUIDED PROCEDURES

(75) Inventors: Ruola Ning, Fairport, NY (US); David L. Conover, Rochester, NY (US); Yong Yu, Fairport, NY (US)

(73) Assignee: Koning Corporation, West Henrietta, NY (US)

( * ) Notice: Subject to any disclaimer, the term of this patent is extended or adjusted under 35 U.S.C. 154(b) by 1336 days.

(21) Appl. No.: 12/342,060

(22) Filed: Dec. 22, 2008

(65) Prior Publication Data

US 2009/0171244 A1    Jul. 2, 2009

Related U.S. Application Data

(60) Provisional application No. 61/016,030, filed on Dec. 21, 2007.

(51) Int. Cl.
  *A61B 6/00*     (2006.01)
  *G06T 11/00*    (2006.01)
  *A61B 6/03*     (2006.01)

(52) U.S. Cl.
  CPC .............. *A61B 6/502* (2013.01); *A61B 6/032* (2013.01); *G06T 11/006* (2013.01)
  USPC .............................. 600/427; 378/37; 382/274

(58) Field of Classification Search
  USPC ........................................ 600/472
  See application file for complete search history.

(56) References Cited

U.S. PATENT DOCUMENTS

| | | | |
|---|---|---|---|
| 4,930,525 A * | 6/1990 | Palestrant | 128/898 |
| 5,595,177 A | 1/1997 | Mena et al. | |
| 5,598,269 A * | 1/1997 | Kitaevich et al. | 356/399 |
| 6,258,104 B1 | 7/2001 | Kreizman et al. | |
| 2002/0156365 A1* | 10/2002 | Tsekos | 600/411 |
| 2005/0080333 A1* | 4/2005 | Piron et al. | 600/417 |
| 2006/0094950 A1 | 5/2006 | Ning | |
| 2007/0270687 A1 | 11/2007 | Gardi et al. | |

FOREIGN PATENT DOCUMENTS

| | | | | |
|---|---|---|---|---|
| DE | 102005012985 | | 7/2006 | |
| WO | WO 2005/067800 | * | 7/2005 | A61B 8/00 |
| WO | WO 2006/119426 | * | 11/2006 | A61B 5/05 |
| WO | WO-2007/141784 A2 | | 12/2007 | |

* cited by examiner

*Primary Examiner* — Tse Chen
*Assistant Examiner* — Patricia Park
(74) *Attorney, Agent, or Firm* — James W. Hill; McDermott Will & Emery LLP

(57) ABSTRACT

Disclosed are embodiments of methods of and systems for detecting and biopsying lesions with a cone beam computed tomography (CBCT) system. The system comprises, in some embodiments, a CBCT device configured to output a cone beam CT image of at least a portion of a patient's breast and a multi-axis transport module, having at least three degrees of freedom and configured to position a biopsy needle within a 3D frame of reference based on inputs received from the cone beam CT device. The transport module can be configured to place the biopsy needle adjacent to, or within, a target of interest within the breast. Also disclosed are embodiments of methods of and systems for testing CBCT systems with phantoms.

16 Claims, 18 Drawing Sheets

METHODS AND APPARATUS OF CONE BEAM CT IMAGING AND IMAGE-GUIDED PROCEDURES

RELATED APPLICATIONS

This application claims priority benefit from U.S. Provisional Application No. 61/016,030, filed Dec. 21, 2007, the entire contents of which are incorporated by reference herein.

FIELD OF THE INVENTIONS

Embodiments of the invention are related to apparatus and methods for use in breast biopsy procedures and other breast cancer treatment procedures guided by cone beam CT imaging.

BACKGROUND

According to the National Cancer Institute, one out of eight women will be diagnosed with breast cancer in their lifetime. In addition, even though recent trends indicate a decline in the incidence of breast, it still remains that each year approximately 40,000 women will die from the disease.

The causes of breast cancer are varied, and as a result there is no single causative factor, making the development of successful treatments difficult. Thus, even though attempts have been made to understand the underlying biological processes involved in the development of the disease, and to potentially control incidence through identification of risk factors, combined with methods of prevention, early detection continues to be widely regarded as the most effective means to improve overall mortality and morbidity.

At present, mammography is generally accepted as the standard and most widely used test for the earliest detection of breast cancer. Despite the widespread use of mammography as a diagnostic tool, it nonetheless suffers from limitations that impact on its usefulness as a diagnostic tool for accurately detecting the presence of potential cancerous lesions. For example, in some groups of women, the sensitivity of mammography can be as low as 30-40%. In addition to false positive reports (report of a tumor where none exist), up to 20% of breast cancers are missed entirely by mammographic screening.

SUMMARY

Embodiments of the present disclosure provided improved methods of breast cancer detection, diagnostics and treatment. The methods described herein provide for increased accuracy and earlier detection than is possible for prior art methods.

In some embodiments, there is provided a cone beam computed tomography (CT) guided biopsy system, for use in detecting and biopsying suspected lesions in a patient, the system comprising: a patient table, configured to position a patient for a breast biopsy procedure; a cone beam CT device coupled to the patient table, the cone beam CT device configured to output a cone beam CT image of at least a portion of a patient's breast; a multi-axis transport module, having at least three degrees of freedom and configured to position a biopsy needle within a 3D frame of reference based on inputs received from the cone beam CT device; wherein the transport module is configured to place the biopsy needle adjacent to, or within, a target of interest within the breast.

In some embodiments, the biopsy needle is configured to sample tissue located at the target of interest. In some embodiments, the transport module further comprises at least one position sensor configured to output information indicative of a position of the biopsy needle, relative to the target of interest. Certain embodiments include at least four degrees of freedom.

In some embodiments, the transport module further comprises at least one position sensor configured to output information indicative of a position of the biopsy needle, relative to the target of interest. In some embodiments, the transport module is further configured to rotate the biopsy needle about a longitudinal axis.

In some embodiments, the system is further configured to determine a distance between an area on a surface of the patient's body, and the target of interest, and to output the distance to the transport module. In some embodiments, the distance comprises a minimum distance among a set of distances from a corresponding set of points of entry on the patient's body, and the target of interest. In some embodiments, the patient table has a primary plane extending along a surface upon which the patient is positioned; further comprising a set of line segments, each of said line segments extending from one of the points of entry to the target of interest; and wherein the set of line segments lie within a plane substantially parallel to the primary plane. In some embodiments, one of the set of line segments has a length substantially equal to the minimum distance and extends along a path that substantially avoids, for example, vessels, fibrous structures, or fibrocystic changes within the breast.

In some embodiments, the path is substantially aligned with a major axis of the target of interest.

In some embodiments, the system further comprises a display module configured to provide a display output representative of a position of the biopsy needle and the target of interest, based on imaging data inputs received from the cone beam CT device, and positional inputs received from the position sensors. In some embodiments, the display module is further configured to display imaging data inputs as at least one of an orthogonal section, an oblique section, a surface rendering, a volume rendering, and navigational data, with respect to the breast.

In some embodiments, the system further comprises a compression module, configured to compress the breast and maintain the breast in a substantially fixed position during the breast biopsy procedure. In some embodiments, the compression module further comprises a movable access window that provides access to the breast for the biopsy needle. In some embodiments, the compression module further comprises a compression plate configured to immobilize the breast against the access window. In some embodiments, the access window is configured to be oriented manually. In some embodiments, the compression module further comprises a guide configured to direct the biopsy needle to enter the patient's body along a path substantially perpendicular to a surface of the patient's body at a region where the biopsy needle enters the body.

In some embodiments, the system further comprises a targeting module, configured to indicate a point of entry for the biopsy needle on the surface of the patent's body.

In some embodiments, the system further comprises a computer-controlled collimator that collimates an X-ray beam emitted by the cone beam CT device.

In some embodiments, there is provided a method, for detection, diagnosis, or treatment of a lesion in a patient's breast using a cone beam computed tomography (CT) guided biopsy system, the method comprising: providing a patient table, configured to position a patient for a biopsy procedure; providing a cone beam CT module, configured to output a tomographic image of at least a portion of the patient's breast; outputting from the CT module a 3D reconstruction of at least a portion of the breast that includes a lesion; determining a path through which to guide a biopsy needle to the lesion, based on the 3D reconstruction; providing a multi-axis transport module, configured to move the biopsy needle along the path to the lesion; moving the biopsy needle from a location outside the patient's body to the lesion; and removing at least a portion of the lesion with the biopsy needle.

In some embodiments, the method further comprises determining a volume of interest, wherein the volume of interest comprises a portion of the breast that includes the lesion.

In some embodiments, the method further comprises providing a computer-controlled collimator, configured to collimate an X-ray beam emitted by the CT module.

In some embodiments, the method further comprises providing a compression module, configured to maintain the breast in a substantially fixed position during imaging and biopsy. In some embodiments, the compression module further comprises a movable access window that can be oriented to provide access to the breast for the biopsy needle. In some embodiments, the access window is oriented such that it provides a path for the biopsy needle having a minimal skin-to-lesion distance; wherein the path begins at an entry point for the biopsy needle on the patient's body; and wherein the path ends within a portion of the breast that includes the lesion.

In some embodiments, the method further comprises visually marking the entry point with a light projected onto the surface of the patient's body. In some embodiments, the compression module further comprises a compression plate, configured to compress and substantially immobilize the breast during imaging and biopsy.

In some embodiments, the method further comprises determining, in the 3D reconstruction, a position of at least one of the biopsy needle, a lesion, a surface of the patient's body, a point of entry into the patient for the biopsy needle, a vessel, and a path between the point of entry and the lesion. In some embodiments, the compression module further comprises a movable access window that is orientable to provide access to the breast for the biopsy needle.

In some embodiments, the method further comprises determining the path such that the biopsy needle avoids large blood vessels in the breast as it is moved along the path to the lesion. In some embodiments, the method further comprises determining the path such that the biopsy needle avoids a physical structure or avoids penetration of the chest wall as it is moved along the path to the lesion. In some embodiments, the method further comprises placing a fiducial marker at a site marking a position indicative of a location of the lesion.

In some embodiments, there is provided a method for performing a cone beam CT guided breast biopsy, comprising: providing a cone beam CT system configured to guide a biopsy needle to a site of a lesion located in a patient's breast, based on tomographic images provided by the cone beam CT system; imaging the breast to detect a lesion; determining a volume of interest, wherein the volume of interest includes a portion of the breast in which a lesion is located; positioning a biopsy needle in a location effective to sample the lesion, based on guidance provided by the cone beam CT system; collimating the cone beam CT to limit a field of view in an image of the volume of interest during sampling of the lesion; determining a needle trajectory, comprising coordinates $P_{entry}(P_x, P_y, P_z, \Delta\theta')$, wherein the trajectory begins at $P_{entry}$, and ends substantially at the lesion; positioning the biopsy needle substantially at the lesion, according to the coordinates $P_{entry}(P_x, P_y, P_z, \Delta\theta')$; scanning the volume of interest to confirm needle position prior to sampling the lesion; sampling the lesion; removing the biopsy needle from the patient; placing a fiducial marker at a site formerly occupied by the lesion; acquiring a post-biopsy image to determine removal of the lesion.

In some embodiments, there is provided a system, for simulating a cone beam CT guided breast biopsy procedure, comprising: a patient table, configured to position a patient for a breast biopsy procedure; a breast biopsy phantom, comprising a simulated lesion; a cone beam CT device that outputs a tomographic image of the simulated lesion within the phantom; a multi-axis transport system coupled to a biopsy device, and configured to position a biopsy needle, relative to a location of the simulated lesion, based on inputs received from the cone beam CT device.

In some embodiments, the simulated lesion has a dimension of from about 10 mm to about 15 mm. In some embodiments, the simulated lesion has a dimension of from about 5 mm to about 10 mm. In some embodiments, the simulated lesion has a dimension of from about 2 mm to about 5 mm.

In some embodiments, the phantom is configured to simulate calcifications arranged in a cluster, the cluster having a size of from about 3 mm to about 10 mm. In some embodiments, the phantom is configured to simulate individual calcifications of a size less than about 0.5 mm. In some embodiments, the phantom is configured to simulate a breast having a plurality of lesions. In some embodiments, the phantom is configured to simulate a lesion less than about 5 mm in size.

Some embodiments provide a system, for simulating a cone beam CT guided breast biopsy procedure, comprising: a patient table, configured to position a patient for a breast biopsy procedure; a breast biopsy phantom, comprising a simulated lesion; a cone beam CT device, coupled to the patient table, that outputs an image of the simulated lesion within the phantom; and a multi-axis transport system coupled to a biopsy device, and configured to position a biopsy needle, relative to a location of the simulated lesion, based on inputs received from the cone beam CT device.

In some embodiments, wherein the simulated lesion has a dimension of from about 10 mm to about 15 mm, and in certain embodiments, the simulated lesion has a dimension of from about 5 mm to about 10 mm. In further embodiments, the simulated lesion has a dimension of from about 2 mm to about 5 mm.

Certain embodiments provide methods, for detection, diagnosis, or treatment of a lesion in a patient's breast using a cone beam computed tomography (CT) guided biopsy system, comprising: receiving, from a cone beam CT module, an input indicative of a 3D reconstruction of cone beam CT data indicative of a lesion in the patient's breast; based on the input, determining a path through which to guide a biopsy needle to the lesion; and outputting machine readable instructions to a multi-axis controller of the biopsy needle, resulting in movement of the biopsy needle along the path to the lesion.

In some methods, the determining the path comprises avoiding a physical structure in the breast, and in some methods, the determining the path comprises determining a distance between an area on a surface of the patient's body and the lesion. Some embodiments provide that the distance comprises a minimum distance among a set of distances from a corresponding set of points of entry on the patient's body and the lesion.

Some embodiments provide a computer-implemented system, for detection, diagnosis, or treatment of a lesion in a patient's breast using a cone beam computed tomography (CT) guided biopsy system, comprising: an input module that receives, from a cone beam CT module, an input indicative of a 3D reconstruction of cone beam CT data indicative of a lesion in the patient's breast; a processing module that determines, based on the input, a path through which to guide a biopsy needle to the lesion; and an output module that outputs machine-readable instructions to a multi-axis controller of the biopsy needle, resulting in movement of the biopsy needle along the path to the lesion.

Some embodiments provide that the path avoids a physical structure in the breast. In some embodiments, the path comprises a length that is a minimum distance, between an area on a surface of the patient's body and the lesion, among a set of distances from a corresponding set of points of entry on the patient's body and the lesion.

DETAILED DESCRIPTION

Figure 1:
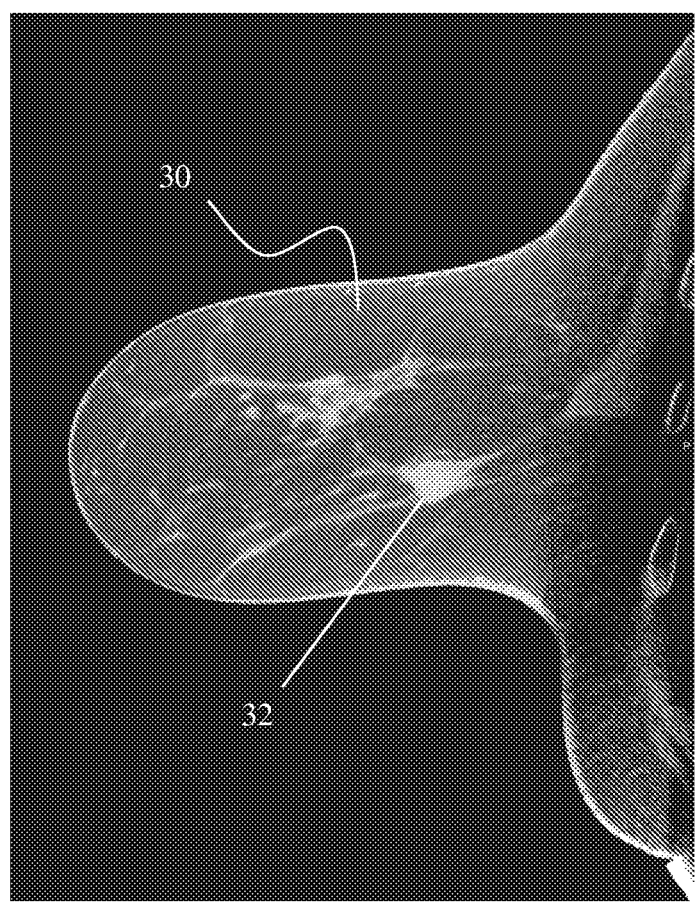
FIG. 1 illustrates an image of a breast acquired by cone beam CT ("CBCT").

Embodiments of the invention are related to a cone beam computed tomography (CBCT) system. CBCT provides many improvements over prior art methods, including permitting the detection of smaller lesions earlier than is possible with existing methods and apparatus. When lesions are detected, a biopsy procedure can be used to sample tissue for characterization with respect to whether a tumor is present, and more specifically, if the tumor appears to be metastatic. In some cases, percutaneous large gauge needle core biopsy (NCB) is an acceptable alternative to open surgical biopsy. Described herein are methods of and systems for detecting and biopsying lesions with a CBCT system.

The following U.S. patents are herein incorporated by reference in their entireties: U.S. Pat. No. 5,999,587 (Ning et al.); U.S. Pat. No. 6,075,836 (Ning); U.S. Pat. No. 6,298,110 (Ning); U.S. Pat. No. 6,477,221 (Ning); U.S. Pat. No. 6,480,565 (Ning); U.S. Pat. No. 6,504,892 (Ning); U.S. Pat. No. 6,618,466 (Ning); and U.S. Pat. No. 6,987,831 (Ning).

Biopsies can be performed clinically where lesions are palpable, or where more accuracy is required, using image guidance. While, it may possible in some cases to perform an NCB using sonography, embodiments described herein disclose the use of CBCT to image lesions, a particular advantage where a lesion is sonographically occult.

A series of phantom studies have been performed. The results of computer simulation and phantom studies indicate that CBCT can detect a 2 mm carcinoma and a 0.2 mm calcification in an average size breast (about 11 cm in diameter at the chest wall) with a total dose of about 500 millirad. This dose is less than or equivalent to that of a single conventional mammography exam, assuming two views are required for each breast.

In a clinical pilot study, 70 breasts were examined. Both normal and cancerous tissue was evaluated. The results of these studies showed that image quality using CBCT (i.e., spatial resolution, low contrast resolution, uniformity, and noise) was excellent, and coverage of the breast, including the chest wall, was at least equivalent to that obtained using standard mammography techniques. In addition, visualization of major blood vessels was very good, even without the use of a contrast agent.

Briefly, the major features of an exemplary prototype include a horizontal ergonomically designed patient table with a modular insert that optimizes imaging coverage of the uncompressed breast and chest wall. There are provided wide openings (1 m) on each side of the patient table for easy positioning of the breast and access for procedures, for example, imaging-guided biopsy, without requiring significant changes to the basic platform. Some embodiments also provide slip ring technology, which facilitates efficient dynamic contrast imaging studies as well as angiogenesis imaging.

Providing the clinician with a tool to detect disease that may not be evident by physical exam or other modalities requires obtaining suspect tissue samples for histological evaluation. This can be done either through needle localization and open surgical biopsy or percutaneous large gauge needle core biopsy (NCB). NCB is an accepted alternative to open surgical biopsy, which can be performed clinically (in palpable lesions) or with more accuracy, by image guidance and is now the standard of care for initial tissue acquisition methods.

All imaging methods, of necessity, provide directional guidance for use with existing percutaneous biopsy devices or vacuum assisted biopsy systems. In the present disclosure, the combination of CBCT imaging with a localization and guidance biopsy system is expected to provide superior results over biopsy systems that use other imaging modalities. CBCT provides an additional advantage in that it provides the clinician with a 3D tool to further investigate lesions of an indeterminate nature that were detected by other methods. In addition, with the enhanced CT dataset provided by CBCT, the clinician is able to biopsy in 3D space.

To compensate for mammography's limitations and to increase the diagnostic yield and further contribute to the overall management of the breast cancer patient, two primary adjunctive modalities have been added to the diagnostic paradigm. Targeted sonography can be used in the diagnostic setting to distinguish fluid verses solid masses and for localization and biopsy. Recent studies have investigated with it is possible to distinguish between benign and malignant masses using a focused ultrasonic exam.

Ultrasound is a low spatial resolution study and is limited in its usefulness in detecting and characterizing calcifications. Since 30-50% percent of non-palpable breast cancers present as microcalcifications without associated mass, and an additional 23% of masses will not be evident by ultrasound, sonography will likely remain an adjunctive rather than primary technology. Thus, while recent studies have illustrated the value of sonography as a screening tool in detecting otherwise occult cancers in some populations (high risk, dense breasts), the positive predictive value is lower than mammography with a higher rate of false negatives. As a result, screening using ultrasound is only advocated for specific populations as an additional screening method.

In addition to the limitations described above, there is no standardized method for screening by sonography and the study is highly dependant on operator skill. Reported mean exam times are from 1-15 minutes (range 2-45 minutes) when performed by an extremely skilled and experienced physician trained in breast disease diagnosis or physician/technologist team.

In contrast, CBCT is a high-contrast resolution and high-spatial resolution modality. Our studies have illustrated its capacity to detect calcifications on the order of 0.2 mm and masses as small as 1-2 mm. While early detection is highly desirable for early breast cancer diagnosis, lesion characterization is at least as important in order to minimize false positives and to increase the overall positive predictive value of breast disease diagnosis. The 3D tomographic image with a $(0.27 \text{ mm})^3$ isotropic resolution (with capabilities of $(0.08 \text{ mm})^3$) can better characterize the morphology of both mass and calcifications. Because image information is provided in 3D space, CBCT can provide a more accurate assessment of the distribution of calcifications and the extent of disease. Also, more of the calcification associated with lesions will be evident as a result of increased contrast, spatial resolution, and lack of superimposed structures. A full 360° 3D volumetric bilateral CBCT study can be completed in less than 5 minutes, providing yet another advantage over current methods for detecting breast cancer.

Currently, intravenous dynamic contrast enhanced breast MRI (CEBMRI) is the only currently available diagnostic tool able to provide functional information that aids in the diagnosis of breast cancer. Because the CEBMRI study has a high negative predictive value, and near 100% sensitivity for invasive breast cancer, it serves as a valuable adjunctive modality in managing the breast cancer patient, once cancer has been diagnosed using other means.

Despite being a tomographic study, CEBMRI does not provide all of the advantages that are available with CBCT. For example, CEBMRI is dependent on contrast resolution provided by perfusion of the tumor neovasculature with intravenous contrast agents. Significantly, CEBMRI imaging is distinguishable from other imaging methods in that it only detects contrast enhancement of vasculature, rather than actual breast anatomy. This dependence on contrast requires balancing spatial resolution against temporal resolution to obtain a reasonable analysis of enhancement kinetics. Thus, despite a 1 mm×1 mm in-plane resolution, CEBMRI has a typical 3 mm slice thickness and depending on the protocol may employ spaces of 2-3 mm between slices, with the result that evaluation of morphologic features suffers.

While CEBMRI is a tomographic technique, its 3D rendering is poor, providing a contrast uptake maximum intensity projection (MIP) used for geographic location only, rather than added diagnostic morphologic data. Also, CEBMRI is not able to distinguish calcifications, which are known to be present in up to 50% of breast cancers not associated with a mass. While BMRI has a high sensitivity for invasive cancers, current techniques may be limited in detecting DCIS, because of its limitations in imaging calcifications and the early neovasculature. The specificity of BMRI varies by report (37%-97%) and protocol methodology, but as the technique becomes more refined, the specificity improves. CEBMRI, however, is primarily limited by its spatial resolution. CEBMRI has been found in most cases to have higher sensitivities than mammography for screening of the high-risk patient. However, the best results are obtained when combined with mammography. To date, a reliable method has not been devised to image a breast specimen after CEBMRI needle localization and excisional biopsy, increasing the likelihood of re-excision to achieve clear margins. CEBMRI obliges substantial burden to patient and staff, either in time, cost or both. The exorbitant cost, procedure time (15-30 minutes per breast), interpretation time and the need for contrast injection, as well as MRI's restrictions (e.g., bore size, coil size limitations, and patient claustrophobia), require prudent use of this technique whether for screening or diagnostic reasons.

The CBCT provides a superior alternative to CEBMRI, independent of intravenous contrast agents. The study offers high spatial resolution 3D tomographic images with a standard $(0.27 \text{ mm})^3$ isotropic resolution (with capabilities of $(0.08 \text{ mm})^3$) and a contrast resolution on the order of 10-fold greater than mammography at a dose comparable to a two-view mammogram. In comparison to CEBMRI, CBCT is a volumetric image acquisition method, resulting in a full true 3D isotropic rendering. Thus, the MIP of CEBMRI is unable to provide the enhanced morphologic data resulting from the 3D dataset obtained by CBCT. Unlike CEBMRI, which entails scheduling, and screening prior to imaging (as well as contrast injection, etc), CBCT can be made readily available as each procedure can be completed in a fraction of the time required for CEBMRI.

Because of the high spatial resolution and exquisite contrast resolution provided by CBCT, calcifications of 0.2 mm and masses 1-2 mm in size can be resolved, characterized, and their distribution determined. Consequently, CBCT provides a number of advantages to detect DCIS, as well as other cancers, and can be used to determine the extent of disease. In addition, as the study is exceptionally robust, with familiar morphologic indices more intuitive to the radiologist, it is reasonable to expect that CBCT can be used as a first line work-up modality to resolve areas of suspicion detected by other means. This contrasts with the two or more 2D mammograms and other adjunctive imaging that is typical standard of care today.

There are now standard CT methods that also take advantage of contrast agents to enhance imaging. In contrast studies employing standard multi-detector-row CT, authors have reported sensitivities of 90%-100% and specificities of 73%-85%. It is likely that functional studies employing contrast agents will be a natural progression in the development and use of CBCT in the overall management of the breast cancer patient. Because of slip-ring technology and control over temporal imaging, contrast enhanced CBCT (CE-CBCT) is more useful, providing the functional imaging of the BMRI exam, but with the exquisite spatial and contrast resolution to provide added morphologic data to the enhancement kinetics. Employing subtraction and other advanced processing, it is expected expect that CE-CBCT provides better results at reasonable dose levels because of the superior contrast resolution reported in absolute density values (HU). The non-enhanced study can be used to better select those patients that can benefit from CE-CBCT.

Comparison of Modality-Based Minimally Invasive Biopsy

Percutaneous large gauge needle core biopsy is an accepted alternative to open surgical biopsy and can be performed clinically (palpable lesions only) or by image guidance. X-ray guided stereotactic and sonography are the most common methods for image guidance, while MRI guided biopsy is reserved for lesions that even after "second look" review with sonography or x-ray remain occult because of its complexity.

Stereotactic breast biopsy (SBB), typically a quick and efficient guidance method, requires dedicated equipment and depends on two angled projection images and triangulation to localize a mammographically visible lesion. This modality is indicated for both mass and calcifications and is limited by superimposition of structures and inadequate contrast discrimination. The 2D projection images of SBB can often require multiple repeat scout and stereo pair images to reliably reproduce the area of interest for biopsy.

Sonographically guided visualization and biopsy requires skill on the part of the clinician and is an attractive alternative to X-ray or MRI guided biopsy as it employs existing sonography equipment and provides real-time visualization of the needle tip, multi-directional biopsy capabilities as well as access to all areas of the breast. Thirty to fifty percent of non-palpable breast cancers present as microcalcifications alone and 23% of masses are not evident using ultrasound. Episodes of bleeding and bleeding requiring treatment beyond extended compression times may be increased with ultrasound-guided biopsy as the breast is not compressed (which reduces the blood-flow) as is typical for other image guided procedures. Although the radiologist has real-time visualization of the needle tip, there is no guarantee that upon firing the needle, accuracy is maintained. One study found that this live nature did not correlate to better diagnostic yield.

MRI guided biopsy has only recently been introduced and compatible non-ferrous equipment is still in development. This biopsy method is hindered by the need to move the patient in and out of the magnet for image-guided biopsy and the very limited amount of working space beneath the coils. Despite the capabilities of BMRI to image the breast and loco-regional area, access for biopsy is problematic and is dependant on the shape and flexibility of the breast coils and biopsy-grid system. Typically, biopsy is restricted to the lateral approach, with medial access devices only just being developed. These two aspects severely inhibit the clinician in biopsy performance. The non-ferrous requirement of biopsy devices prohibits the use of a spring-loaded component typical of breast biopsy devices, which gives CBCT guided biopsy (CBCT-GBx) an advantage, as CBCT-GBx does not suffer from this limitation. In addition, BMRI requires a contrast injection and imaging sequences can take as long as seven minutes for both localization and targeting, and then verification of accuracy (typically through an obturator method) for biopsy. Because of the complexity and the increased physician and technologist procedure times of the BMRI-Bx (an hour or longer is typically scheduled), the clinician will typically perform focused sonography or x-ray imaging for a BMRI detected lesion, adding cost and time burden and another visit. Only if the lesion remains occult on these imaging methods will the radiologist resort to MR guided biopsy.

The CBCT-GBx system 28 is a prone biopsy system, which merges embodiments of the CBCT system with embodiments of add-on localization and guidance (LG) packages. The CBCT-LG approach in some ways replicates the simplicity of embodiments of stereotactic techniques (and so is intuitive to users) with the many differences, including its imaging capabilities. The CBCT imaging capacity significantly reduces cancellation of biopsy due to lesion non-visualization and provides for a more efficient breast biopsy with less maneuvering and imaging of the patient. The CBCT Imaging provides unprecedented access to all areas of the breast 30 including the chest wall (FIG. 1) as compared to SBB, BMRI and ultrasound guided biopsy. Thus, a single low-dose acquisition provides a reliable and reproducible volume of interest suitable for imaging and sampling of both calcifications and masses 32.

In some embodiments, the clinician and technologist have available 3D rendering and tomographic slices for unparalleled lesion visualization and targeting. Embodiments herein include an x, y, z, coordinate approach, which provides at least three degrees of freedom, and some embodiments provide at least four degrees of freedom, which can include a theta angle, a unique and novel additional degree of freedom for biopsy approach. The additional degree of freedom allows the clinician to determine a trajectory path to the lesion that avoids puncturing vessels (which are exquisitely visualized in the CBCT scan) and study complicating or study ending hemorrhage.

Figure 2:
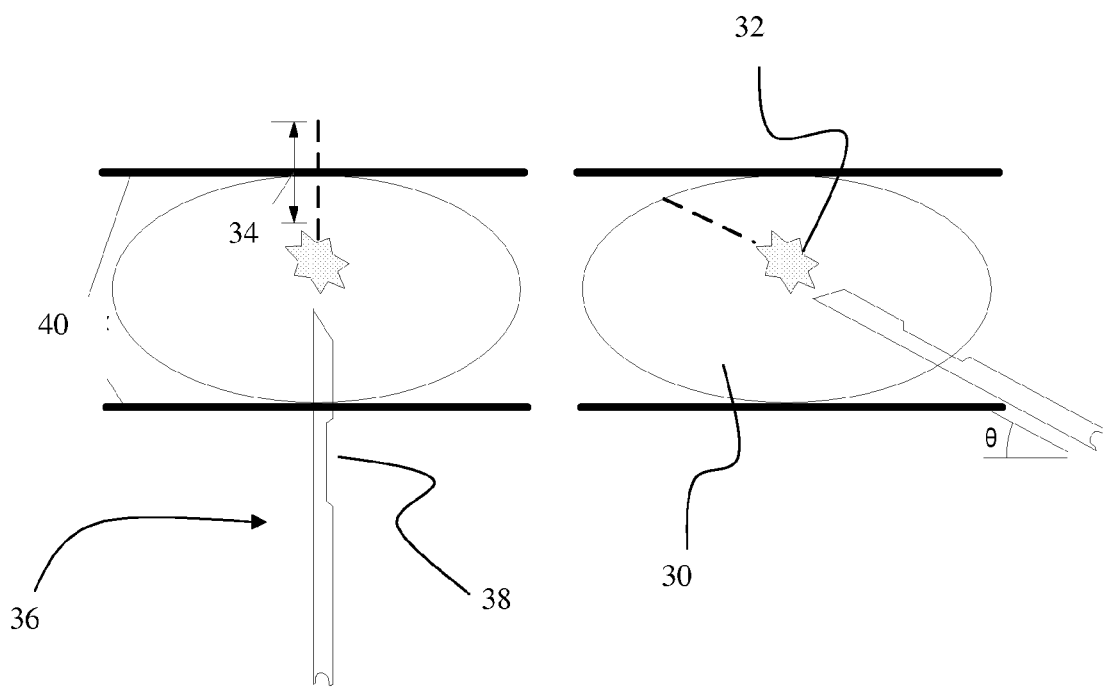
FIG. 2 illustrates a schematic view of embodiments of a biopsy system, showing a fourth degree of freedom, angle theta (θ), for approach during needle biopsy.

The theta ($\theta$) angle approach provides additional space in thin breasts to accept the stroke 34 of the biopsy needle 36 and, in vacuum-assisted devices, allows the trough 38 of the needle 36 to be fully inserted into the breast 30 for adequate prime and biopsy. In addition, the theta ($\theta$) angle allows the needle 36 to traverse in the longest dimension of the lesion, which can increase yield in biopsy specimens (FIG. 2). Also depicted in FIG. 2 are compression plates 40 that are used to stabilize and compress the breast 30 during imaging and biopsy. In some embodiments, the theta ($\theta$) angle is measure by the angle that the biopsy needle is tilted within a coordinate plane from one of the coordinate axes. This may be an offset angle with respect to an original orientation of the biopsy needle, or in some embodiments, the angle is an angle that the biopsy gun is directed prior to operation. In some embodiments, the angle theta ($\theta$) can be an angle that the system is rotated about the breast or target tissue.

Figure 3:
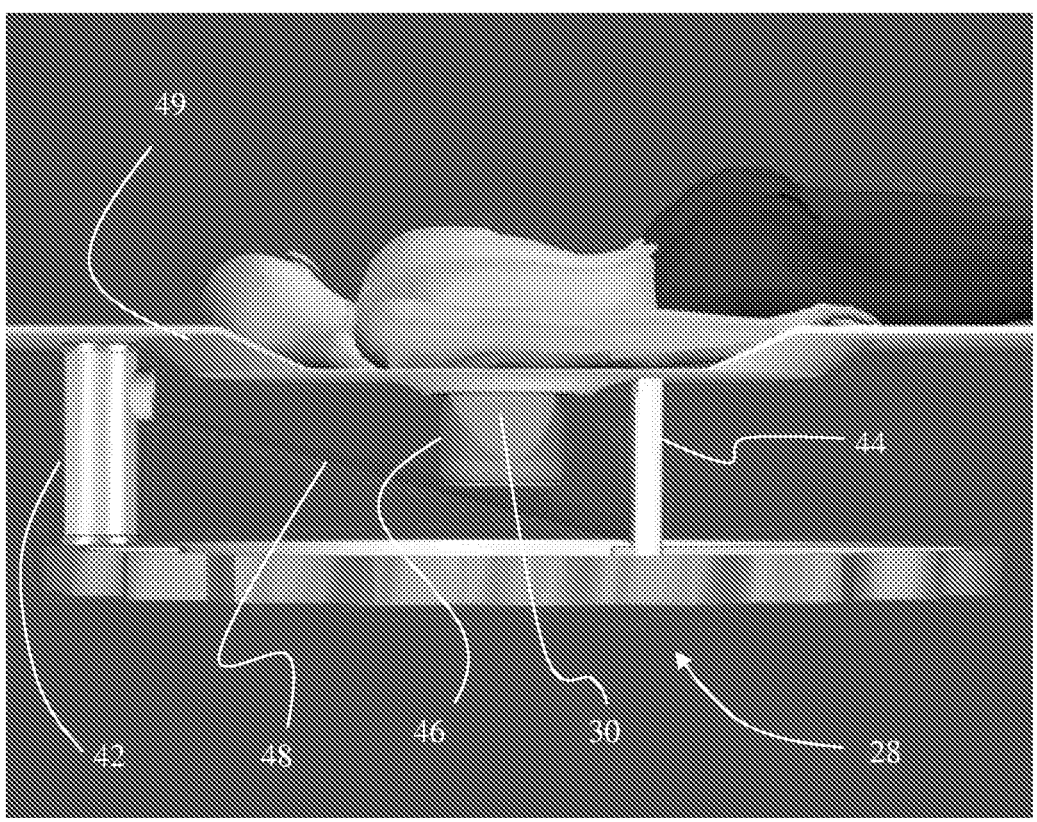
FIG. 3 illustrates embodiments of a patient table and CBCT device for use in breast imaging.

Cone Beam CT-Localization and Guidance System Description of Cone Beam CT System FIG. 3 illustrates exemplary basic components and principles of the system 28. The CBCT scanner system comprises one X-ray source 42 (e.g., Rad 70 [Varian Medical Systems, Salt Lake City, Utah]), which emits a beam 48, and one flat panel detector 44 (FPD) (e.g., PaxScan 4030CB [Varian Medical Systems]) mounted on a rotating assembly. The FPD is specifically designed to meet the needs of cone beam x-ray imaging applications. A patient table 49 is mounted above the rotating tube/detector assembly. The table has an opening that allows the patient's breast 30 to hang pendant in the imaging volume 46 at the rotation axis. The tube/detector assembly rotates around the rotation axis and acquires multiple 2D projection images of the uncompressed breast 30 located at the rotation axis. A 3D volume of the breast 30 can be reconstructed from this dataset of 2D images. Since imaging of the tumor 32 and biopsy needle 36 can be local, collimation can be used to limit the region of exposure to the breast 30 thus significantly reducing dose for subsequent position validation scans.

The patient table 49 is ergonomically shaped and able to be moved vertically so that the underside of the patient table can be about 5 feet, and range from between about 3 feet and about 6 feet, from the floor to facilitate breast 30 positioning for optimal coverage (especially near the chest wall and upper outer quadrant of the axillary region) and biopsy. The tube/detector assembly also is able to move vertically to allow the system to take images for alignment or biopsy needle 36 placement assistance and verification with the patient table at maximum height. Table 1, below, shows examples of CBCT scanning parameters. The parameters of Table 1 are merely examples, and other values can be used and the ranges can be adjusted to extend beyond listed ranges. It will be appreciated by one of ordinary skill in the art that many dimensions and parameters discussed herein can be adjusted to be operable within a range of between about 10% and about 20% of an exemplary value, and in some embodiments, the dimensions and parameters can range less than about 10% or more than about 20% of exemplary values. The covers on the scanner protect the patient and clinicians from mechanical, electrical and radiation hazards during a scan while allowing 1 meter wide access simultaneously from both sides of the patient during a biopsy procedure.

TABLE 1

Cone beam CT scanner parameters

| | |
|---|---|
| Scan time | 5-10 seconds |
| Voxel size | $(0.08\text{-}0.28 \text{ mm})^3$ |
| Dose | About 5 mGy (normal size 50/50 breast) |
| Magnification | 1.42 |
| Pixel pitch | 0.194 mm (0.388 mm with 2 × 2 binning for 30 fps) |
| Dynamic range | >16-bit |
| Projection number | 300 |
| Data acquisition rate | 30 fps (with 2 × 2 binning) |
| Coverage | (16 cm × 28 cm × 28 cm) |
| Reconstruction time | <3 min |

Figure 4:
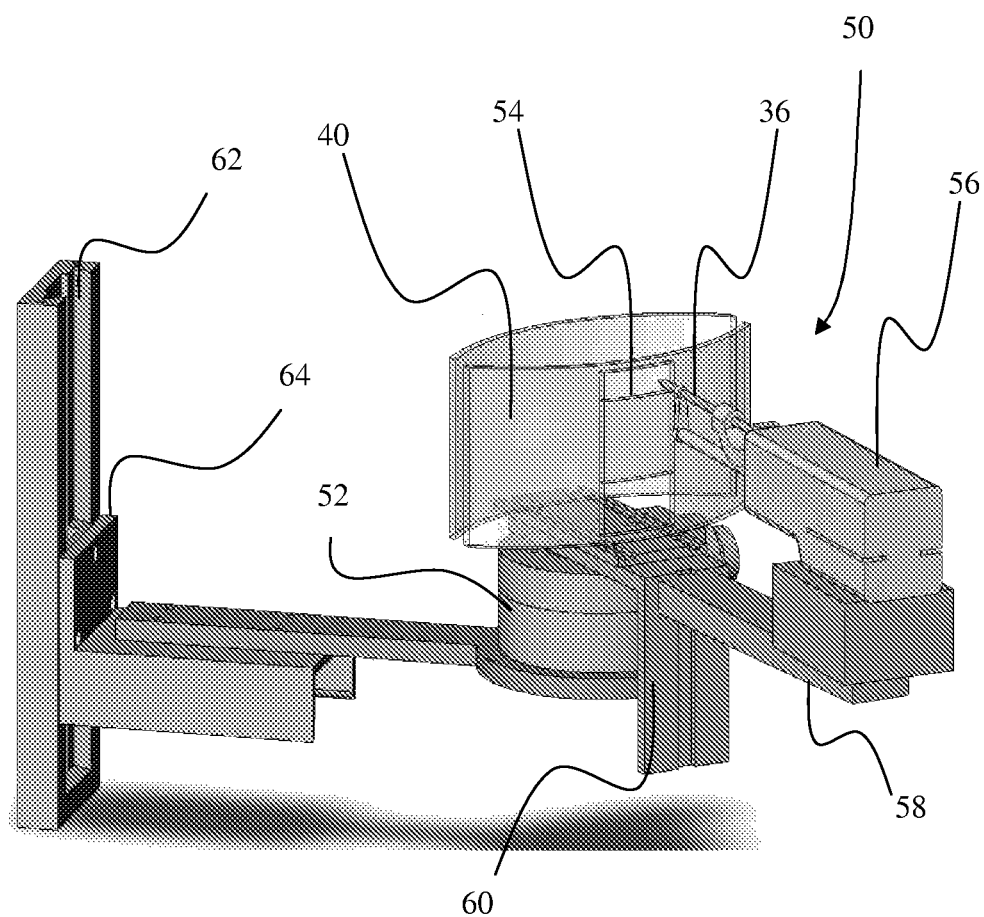
FIG. 4 illustrates embodiments of a CBCT guided biopsy ("CBCT-GBx") system.

Embodiments of a motorized x, y, z, theta stage assembly for CBCT-GBx with orbital motion is illustrated in FIG. 4. Illustrated is an approach that is similar to proven technology of the stereotactic biopsy but tailored to the CBCT system. This system comprises an orbital 4-axis transport system upon which can be mounted the biopsy gun 56, and a rotary stage on which the access window compression assembly can be mounted. The orbital 4-axis transport system can provide 360° rotation around the breast 30 and give a certain amount of travel at given speed and accuracy in x, y, and z as well as +/−90° of rotation of the biopsy gun parallel to the under side of the table. In some embodiments, the system is configured to prevent, or reduce, angular or linear movement that would results in penetration of the chest wall by the biopsy needle 36.

In some embodiments, the vertical (z) stage can provide about 25 cm of vertical travel. This assembly can be accurately located either on the patient table frame or from the tabletop. The assembly can be easily, precisely, and accurately mounted to the patient table and later removed for normal imaging procedures. The assembly can be sealed such that fluids do not enter the electro-mechanical structure and to allow ease of cleaning.

For biopsy purposes, an X-ray translucent compression plate 40 and frame assembly can be used to capture the breast 30 from both sides by motorized mechanism with set compression force and hold it steady with minimal compression. A thumbscrew mechanism allows the technician to complete the compression process. This access window/compression/stage assembly can be mounted on the bottom of the patient table to a rotational bearing 52 with a quick-release locking mechanism. The assembly can be configured to have the ability to revolve around patient's breast 30 to provide flexibility in rotational position around the breast 30 to achieve safe and effective localization with the shortest skin-to-lesion distance. As depicted in FIG. 4, the system can include an access window 54 in a compression plate 40 to allow the needle 36 to extend therethrough during the biopsy procedure. The biopsy needle 36 can be integral with or coupled to a biopsy gun 56 that is configured to received computer and/or machine instructions to actuate the needle 36. The biopsy needle 36 can further be coupled to a lateral track 58 and a vertical track 60 that are configured to adjust positioning of the needle 36.

In some embodiments, an orbital multi-axis (for example, a 4-axis system with X, Y, Z, and theta (θ) movements, or degrees of freedom) motorized transport system 50 with encoder position feedback that holds the biopsy device automatically positions the biopsy needle 36 based on localization data obtained from the 3D CBCT scan. The biopsy device support on the transport system can be designed to be compatible with commercially available percutaneous breast 30 biopsy systems. The transport system 50 can include, among other things, the biopsy gun 56, the lateral track 58, the vertical track 60, the rotational bearing 52, and/or other components, such as positioning sensor and motors, for positioning the needle 36. The orbital 4-axis transport system allows the typical x, y and z movements for localization, and also provides an additional degree of freedom, right/left angular motion parallel to the bottom of the patient table providing unprecedented control over biopsy approach.

In some embodiments, the orbital 4-axis transport system 50 can be mounted to the existing patient table (insert ring or frame) which can be programmed to move a stage to a position dictated by a 3D coordinate determined from a volume matrix produced from the CBCT scan while avoiding defined structures. This includes aiming the needle 36 to provide a trajectory to the biopsy site that is, for example, the shortest skin-to-lesion path, avoids any major vessels within the breast 30 along the needle's trajectory, and avoid puncturing the chest wall. Software and hardware limits can be included to ensure that the needle 36 does not puncture the chest wall. This includes the use of the knowledge of the location of the chest wall in the reconstructed 3D space, trajectory and throw of the needle 36 as well as calibrated look-up tables of various lengths of needles and various vendors' biopsy guns 56 mounted on the transport system's stage. Critical position inputs can be determined from the reconstructed volume such as breast volume, biopsy site and major vessels.

In some embodiments, the transport system 50 is movable with respect to the patient table 49 along, for example, a table coupling track 62 with a bracket 64 that can permit vertical adjustment of the transport system 50, as depicted in FIG. 4. In other embodiments, the transport system 50 is not movable in the vertical direction with respect to the patient table.

In some embodiments, the support stage can be easily mounted and precisely, accurately located to an initialization position and easily removed from the scanner for normal imaging procedures, provide control software for half scan data acquisition control, and provide safety features associated with half scan data acquisition. The biopsy gun mounting plate can also include anterior and posterior guides to support the biopsy needle 36 as well as the thin wire for needle localization and surgical clip introducer (after biopsy). In some embodiments, where the scanning of the actual needle position proves difficult, optional introduction of an obturator to the tumor site, imaging for position verification, then introducing the biopsy gun 56 and needle 36 can be used. Those of skill in the art will be able to readily determine the method to be used.

After CBCT data acquisition, the projection images can be processed to obtain the 3D rendering of the breast 30 along with the coordinates of the suspicious mass with respect to the access window in order to guide the biopsy needle 36. In some embodiments, the coordinates may be provided with respect to another point of reference (e.g., an initial point of the biopsy needle, an origination point of the transport system 50, etc.). 3D display software can provide full visualization. Graphics hardware can be utilized to display very large data sets at interactive speed. Automatic and interactive segmentation tools can support processing of 3D image data. Some embodiments include the ability to view orthographic and oblique sections, surface and volume rendering, as well as tools for data analysis and virtual navigation. These features allow one to fully visualize the true isotropic volume data, and provide accurate visualization and the ability to make precise measurements to localize the breast tumor, major breast vessels, and the biopsy needle trajectory to provide near real-time feedback to guide the biopsy procedure. In some embodiments, the system can be specially designed for cone beam image-guided localization and biopsy.

Embodiments of CBCT Image-Guided Transport System

Figure 5:
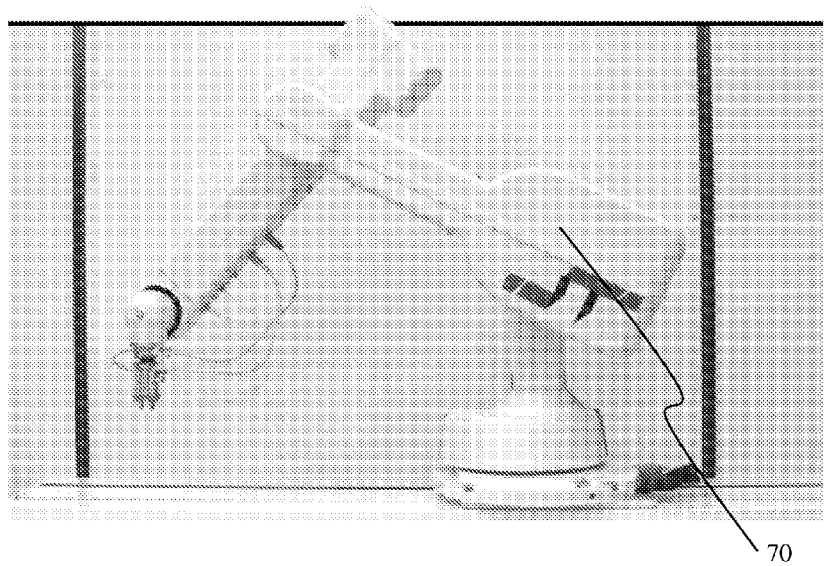
FIG. 5 illustrates an exemplary robotic arm for use in embodiments of CBCT systems described herein.
Figure 6:
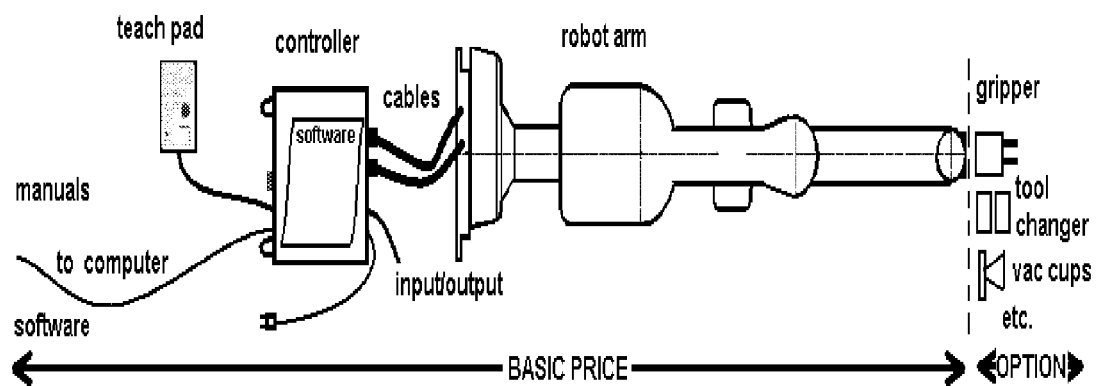
FIG. 6 illustrates an exemplary arrangement of robotic arm and controls for use in embodiments of CBCT systems described herein.

Various methods for the mechanism to transport the biopsy gun 56 and needle 36 to the breast surface at the point where the needle 36 can be introduced through a small aperture in the skin to the tumor site have been introduced and utilized. Many methods include hand-held devices or motorized slides. Because of the CBCT system's high accuracy in 3D space of identifying the central location of a suspicious mass and extent of disease, a more accurate and more flexible approach can be provided. Also, after verification of position, small rotational changes of the needle position may be needed to more completely sample a suspicious volume, ideally without needing to remove and reinsert the biopsy needle 36. This is possible for small orthogonal or rotational movements with the biopsy needle 36 within the breast 30 given the elasticity of the breast tissue. This is important for not only the efficiency of the biopsy sampling but also to minimize the trauma to the breast 30 that needle 36 removal, new skin nick, and reinsertion through new breast tissue would produce. In addition, space underneath the patient table 49 is confined so that a small, articulated transport system is required. A robotic arm 70 could provide a solution for these requirements, for example, like that depicted in FIGS. 5 and 6.

In an exemplary embodiment, robotic arm functionality could be provided by, for example, the R17 5-axis articulated format robotic arm (e.g., Sands Technology International Inc. t/a ST Robotics, Trenton N.J.). The R17 is a complete self-contained five axis vertically articulated robot arm system designed as a cost effective solution for processes requiring long flexible reach or difficult access as required for efficient biopsy of masses in random positions in various size breasts in 3D space. This format is also referred to as anthropomorphic because of its similarity with a human arm. It is a low cost robotic arm, which is fast, accurate, light-weight, and reliable. The robotic arm has rugged, abuse proof construction with smooth, swift, and accurate digital positional control. Its multi-processor controllers have modular electronics, high speed drives and extensive and expandable input/output capability.

A robotic arm 70, such as the R17, can have about a 30" reach and 5 axes of motion, weigh about 48 lbs, has a repeatability of about 0.2 mm, has a mean time before failure of 10,000 hours and can have a payload of up to 7 lbs. This robot can be docked on a rotational ring to get to the best entrance position to the target. It is easy to apply and program yet is capable of intricate tasks thus making it compatible with the accurate 3D mapping produced by CBCT. It has a long reach and therefore a larger and much more useful workspace than comparable machines. The mechanics are simple and reliable, there being R17 robotic arms that have run three shifts a day for ten years without failure. Modification can include the Mk5 package uses new light weight, high speed, high efficiency stepping motors with encoder feedback. The Mk5 package includes the new Mk5 controller which is simple and reliable using a partnership of fast CPU and DSP processors and compact micro-stepping drives.

Input/output features can be included in some embodiments, to detect changes in temperature or pressure for example. In some embodiments, the hand terminates in a mounting plate provide easy mounting of tools, such as grippers and sensors so that it could be easily modified to accept a mounting platform to support a variety of commercial biopsy guns 56 or minimally invasive therapy tools. It is fully enclosed making it easily cleaned to be suitable for being in a biopsy environment. It can be positioned in Cartesian coordinates (reverse kinematics) that would be provided by the CBCT imaging system. Dialog boxes permit positioning in absolute or relative coordinates. Examples of specification of a robotic arm are provided in Table 2 below.

TABLE 2

| Specifications of an Example Robotic Arm | |
|---|---|
| Drives: | High power micro-stepped stepping motors, incremental encoder feedback |
| Reach: | 750 mm/30 ins |
| Payload: | 3 Kg/7 lbs at flange (repeatability figures degrade). |
| Speed (standard drives): | Shoulder 100 deg/sec, Elbow 180 deg/sec, Waist 120 deg/sec. (around 2000 mm/sec multi-joint) |
| Max torque for hand pitch or roll: | 4 Nm (repeatability figures degrade). New - doubled rating |
| Repeatability: | +/−0.2 mm |
| Acceleration: | 2-3 G |
| Weight | 22 Kg/48 lbs (robot only) |
| Power: | 110/240 v ac 420 VA (standard controller) |
| MTBF: | 10,000 hours |

In some embodiments, MOVE or MOVETO commands can be entered or included in a software or firmware program. Wrist/hand angles may be specified or controlled. The robot systems can be programmed in ROBOFORTH II, which is an exemplary robot programming language. There are other alternatives to the use of a fully automated approach to enable a 4-axis transport system to place the biopsy gun in position.

One approach can be to use a breast compression/access window 54 to hang from a bearing mounted to a metal ring that is attached around the hole at the bottom of the table 49. Embodiments of the patient table 49 as described herein can include space and mounting holes for the metal ring. In some embodiments, this metal ring can already be part of the table for the safety cover. Visualization software from a diagnostic scan can be programmed to indicate the best angular position of the breast compression/access window 54 for minimal skin-to-lesion distance. The system 28 can be configured to allow the clinician to manually rotate the compression/access window 54 to this position with the aid of degree-markings on the ring. The bearing can then be manually locked in place and the breast compression/access window 54 manually tightened to secure the breast 30. Another scan can be done to locate the lesion in the presence of the breast compression/access window 54. Based on the 3D coordinates of the lesion, the light from a low power target laser would be guided by a set of servo-galvanometers to that point on the breast surface such that a stylet inserted substantially perpendicularly, for example, to the skin surface would lead it to a desired position (e.g., about 2 mm below a suspicious mass).

A guide can be included on the breast compression/access window 54 to ensure, when desired, substantial perpendicular entry into the breast 30. The depth can be determined from 3D visualization and the depth of the stylet can be set and controlled by the O-ring on the introducer, as can be done in MRI biopsies. The stylet can be removed and the obturator placed through the introducer to the lesion site. Another scan can be performed to verify the obturator's position at the lesion site. The obturator can be removed and the biopsy gun's needle placed through the introducer to the lesion site where vacuum-assisted biopsy is performed and biopsy clips are inserted. After biopsy, another scan can be done to verify biopsy and clip placement. Hand-held biopsy is a common procedure and with embodiments of the CBCT system described, near real-time visualization guidance would become very reliable. Lower dose scans can be performed for this procedure if image quality in the presence of more noise is sufficient to resolve the lesion. Effective noise correction software can be effective to provide suitable image quality.

Servo-galvanometers in confocal scanning laser microscopy and their accuracy and precision allow raster scanning with sub-millimeter precision over lumps of cells. In some embodiments, one low cost laser and a set of 3 or 4 servo-galvanometers can be effective to cover the whole breast 30.

In some cases, a grid system, similar to those used in MRI, can be used in connection with the described embodiments. The CBCT scan can visualize which grid location to place the sub-grid needle guide. The biopsy procedure could then continue as described above. An access window approach instead of the grid can be advantageous in detecting lesions just at the frame portion of the grid or needle guide. In some embodiments, both a grid systems and an access window may be implemented in the system.

Novelty and Advantages of Cone Beam CT Localization and Guidance System

In some embodiments, methods for performing biopsies, or other procedures, can include the following steps, features, and advantages. The CBCT provides a fast, low-dose targeted field of view scan for localization, needle 36 placement and verification of biopsy. Through precise positioning, as described above, higher quality biopsies can be performed including the ability to see and avoid large vessels. This can improve the confidence of the physician for biopsy needle placement at the lesion site, and 3D assessment of the post-biopsy CBCT scan can provide a more accurate verification. No contrast is required to visualize small tumors and large vessels, but, when desired, contrast can be used in some embodiments. There is a reduced time for reconstruction and verification (<3 minutes).

The system provides higher-resolution visualization, than many other procedures and systems, to better characterize calcifications and their distribution and spatial relationships with other structures in 3D space. The system can provide relative comfort to the patient without compromising coverage up to the chest wall through the ergonomic shape of the patient table and a comfortable curved breast holder that stabilizes the breast 30 without hard compression. Because targeted collimation can be used (not exposing the whole breast), a low dose exposure with less scatter can provide better scatter estimation for scatter correction thus improving image quality.

Embodiments of the CBCT image-guided biopsy system can further provide a platform to, among other things: (1) develop automatic collimation for the targeted scan and reconstruction; (2) optimize reconstruction software to reduce metal artifacts in the image due to the biopsy needle; (3) develop better and more accurate computed aided diagnosis (CAD) algorithms; and (4) in some embodiments, serves as an accurate tumor response monitoring tool.

The CBCT image-guided biopsy system is an expandable platform that can be made compatible with minimally invasive treatments (ablation-RF, cryo, HIFU) useful in treating cancerous lesions. In addition, CBCT provides a more precise evaluation of suspicious masses for improved cancerous tumor specificity and tumor angiogenesis.

Further advantages of the CBCT system include providing a true 3D description of breast anatomy and lesions. The system also eliminates, or significantly reduces, overlap and removes, or significantly reduces, superimposed structures, thereby, allowing improved targeting of tumors. The CBCT system allows, with the accurate imaging and precise biopsying capabilities, biopsy of breast cancers in their earliest stages. The system results in greater diagnostic yield due to superior contrast detectability and allows for initial diagnostic imaging and biopsy of suspicious lesions in the same setting. The systems also improves sensitivity and specificity of core biopsy by virtue of improved targeting, and improved targeting can result in reduced sampling error and more definitive diagnosis. The system can also make utilization of percutaneous biopsy more efficient, saving biopsy for those patients whose pathology cannot be reliably diagnosed non-invasively (i.e., masses whose morphologic and contrast enhancement characteristics strongly suggest malignancy).

In some embodiments of a method of CBCT-guided biopsy (CBCT-GBx), the patient lies prone, with feet at either end of the table 49 and the breast 30 pendent through a table aperture. The CT gantry revolves horizontally beneath the patient table; two doors on either side of the gantry open to give clinician and technologist working space between the x-ray tube and detector. The table 49 elevates so that the biopsy team can work beneath the table surface to access the breast 30. The gantry doors are closed for imaging only while the patient remains in-situ for the entire length of the procedure. Once positioned, the patient/table is generally not moved between imaging and biopsy related tasks, which allows in-situ biopsy and on-line needle verification imaging. The table design and aperture has a soft malleable, but cleanable circumference that allows the patient's chest wall and shoulder to drop below the table surface for access to the area of the mammary gland and the loco-regional area. In some embodiments, the table is modified to allow full access to the axilla.

The described access window/compression and orbital 4-axis transport system can travel 360° around the breast 30 from the vantage point of the operator. In contrast to BMRI guided biopsy, and with near-line 3D volume imaging, this provides for 360° approach to the breast 30 in order to obtain an optimal biopsy approach path, which can be, for example, the shortest skin to lesion distance, and offers flexibility for the biopsy. A 3D tomographic volumetric acquisition can be accomplished in under 10 seconds in full scan or half-scan mode for near real-time 3-dimensional confirmation of the needle tip in the horizontal, vertical and depth directions.

Depending on clinician preference and lesion characteristics, the CBCT-GBx system can allow for at least two methods to confirm on-line needle placement accuracy. The first method is where the biopsy needle 36 is imaged in the breast 30 at a pre-fire position. This method uses a half-scan imaging approach. A second method provides for an obturator approach, which employs a full scan acquisition. CBCT-LG can provide on-line display of biopsy accuracy through needle verification in 3D space. The biopsy instrument/needle can be fixed in place on a motorized stage providing unprecedented control and confidence of biopsy needle placement.

The mechanical design of the access window/compression assembly and orbital 4-axis transport system incorporate, in some embodiments, percutaneous core (spring-loaded gun or vacuum assisted) breast biopsy devices. The access window/compression assembly and orbital 4-axis transport system can modularly attach to the bottom of the patient table 49 or table frame with, for example, a simple quick-release mechanism. The breast access window/compression assembly and orbital 4-axis transport system can be configured to be able to revolve around the patient's breast 30 to provide flexibility for the end user to achieve safe and effective localization and biopsy including: shortest skin to lesion distance, vessel avoidance, and facilitate tumor access. In some embodiments, the access window 54 comprises a 5 cm×7 cm aperture into which the biopsy needle 36 (or a needle localizing introducer/obturator, biopsy clip introducer, or localizing wire introducer) can be inserted under CBCT image guidance. The access window 54 can be configured to be able to be positioned to allow needle 36 access to the upper, middle or lower part of the breast 30 while maintaining sufficient compression of the breast 30.

A compression plate 40 can be used to gently immobilize the breast tissue against the access window 54 for reduction of motion artifacts and accurate needle 36 guidance. The design is effective to ensure that the set-up can be performed in only a few minutes. The device can be cleaned with a germicidal agent to limit spread of infection between patients. Both the access window 54 and opposing compression plate 40 can be made of materials that are comfortable for the patient and have low X-ray attenuation to minimize any reconstruction image artifacts.

Figure 7:
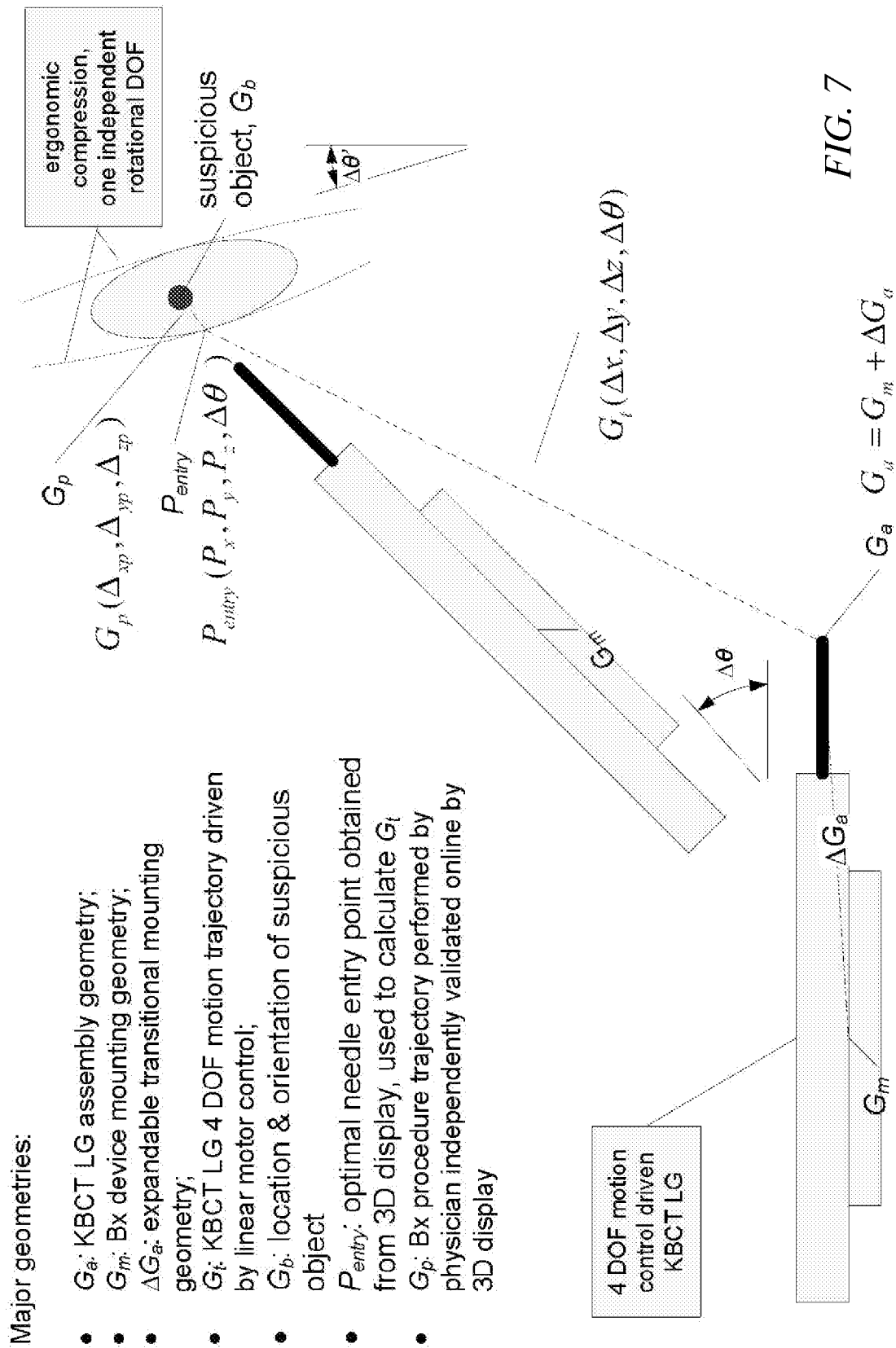
FIG. 7 illustrates an example of motor geometries used in a CBCT guided biopsy system.

The breast 30 can be stabilized in the access window/compression assembly by providing moderate compression, for example, symmetrically applied the breast 30. The reconstructed 3D space provides the exact position of the lesion within the scanning volume. These coordinates can be used to determine the optimal rotational position of the access window 54 on the breast 30. A cone beam CT 3D guidance algorithm can allow determination of the optimal orbital position and x, y, z, theta and needle depth coordinates to drive the orbital 4-axis transport system in order to gain efficient, or desired, access to the target lesion, as illustrated, for example, in FIG. 7. Depicted in FIG. 7 are embodiments of determining appropriate x, y, and z coordinates for performing a biopsy procedure and for determining an approach angle, theta, for the procedure. The orbital 4-axis transport system can be designed to provide vertical motion independent of the access window/compression assembly. The biopsy tools can be supported at two positions along the tool (fore and aft) to provide stable guidance during insertion. Those of skill in the art will appreciate that the actual location of the final position of the biopsy needle position with respect to the lesion can be experimentally validated using phantoms.

A CBCT scan can be used to verify accurate positioning of the biopsy needle 36. Once correct targeting is confirmed, tissue sampling can be performed using a vacuum-assisted breast biopsy device through a coaxial sheath. Sampling can be performed in the direction of the lesion. When tissue sampling is complete, the probe can be retracted and a site marker placed through the coaxial sheath. A final CBCT image of the biopsied region can be performed to verify the location of the sampling artifact and of the site marker. Pathology can be confirmed by methods known in the art. This system can thus provide true in-situ motorized localization and guidance capability for the purposes of biopsy and other minimally invasive procedures. In some embodiments, the site marker, or fiducial marker, can be used in later follow treatment or diagnosis of the lesion. For example, providing a fiducial marker makes it easier to find with precision the site of a lesion that has been biopsied, making it easier for a surgeon to excise the area once the pathology of the lesion has been determined, should follow-up surgery be indicated. Alternatively, where it is thought that the biopsy procedure itself was successful in removing an entire tumor mass 32, the marker provides a precise location of the former location of the tumor 32 for use in later imaging to determine whether or not the mass was completely removed (i.e., should cancerous cells reappear at the site where the biopsy was performed).

In some embodiments, the breast access window/compression assembly and orbital 4-axis transport system can (i) support percutaneous core breast biopsy devices and revolve around patient's breast to provide flexibility for the end user and (ii) achieve safe and effective localization and biopsy, and (iii) allow true in-situ motorized localization and biopsy capability.

Scan and Reconstruction Protocols

Data acquisition protocols and reconstruction protocols can be implemented, in some embodiments, to accurately verify the position of biopsy needle 36 before sampling. In some embodiments, a protocol can include, for example, the following:

1. Scan the compressed breast 30 with the breast access window/compression assembly in position: To indicate the exact position of a suspicious mass in space, a full scan is useful to obtain an accurate reconstruction. A cone beam CT reconstruction algorithm for full scan can be used for this step. In order to ensure safe and effective biopsy, it is advantageous for the radiologist to know the trajectory of the biopsy needle 36 before actual insertion of the biopsy needle 36.

2. Optical method to visually verify position with the biopsy needle 36 in place at the breast surface.

Figure 8:
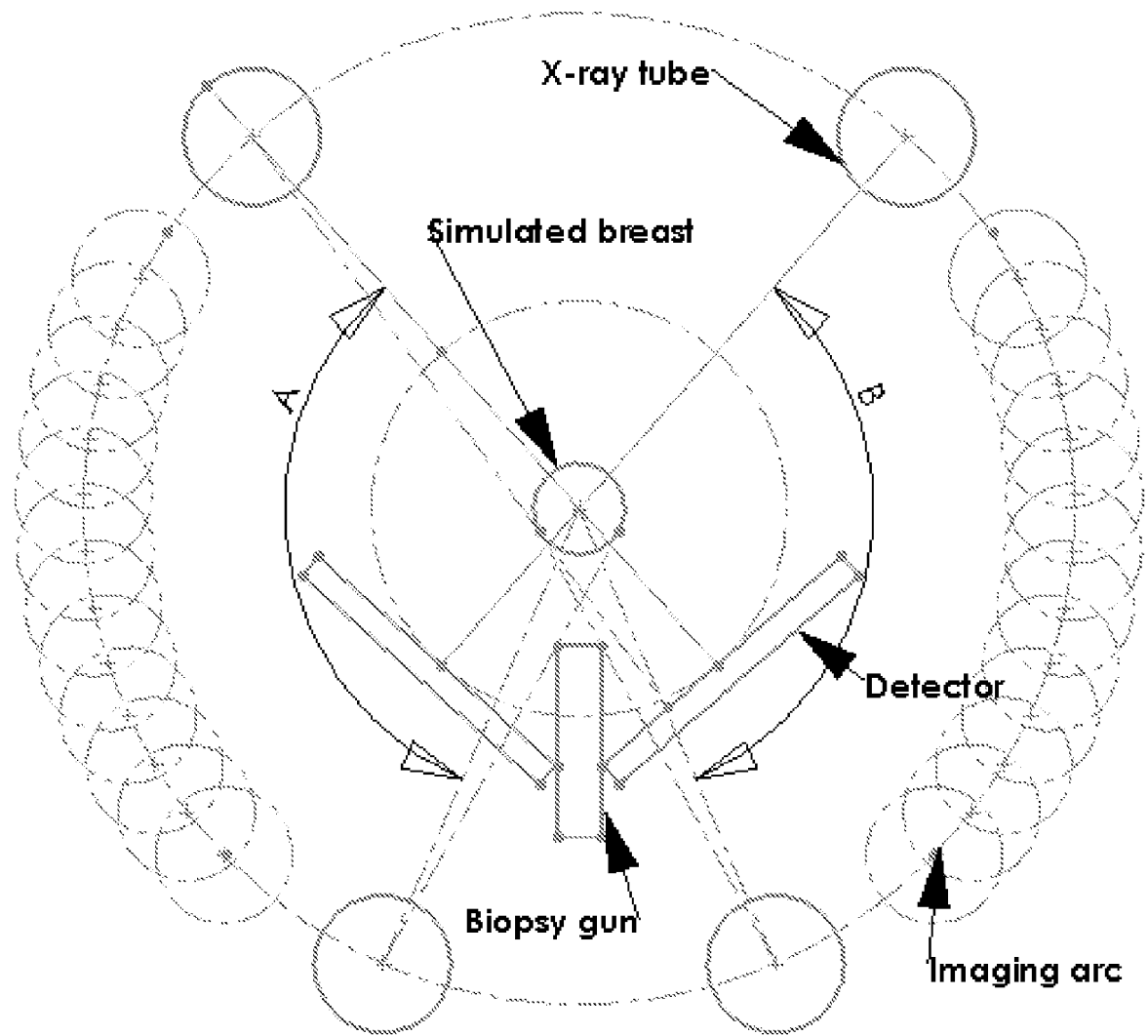
FIG. 8 illustrates embodiments of scan geometries used during CBCT-GBx procedures.
Figure 9A:
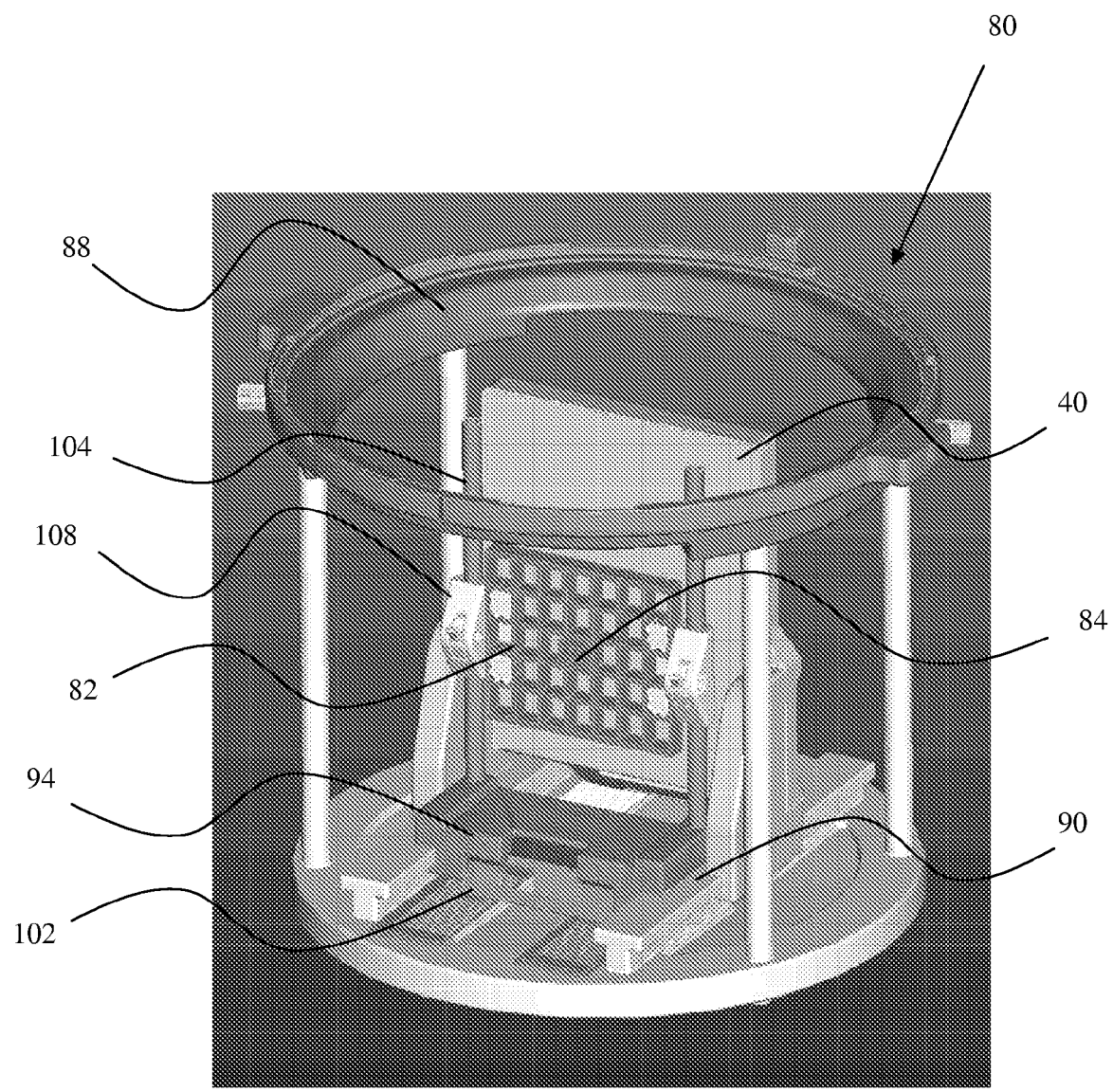
FIGS. 9A-9D illustrate embodiments of a clamp device incorporating a grid clamp within a frame subassembly.
Figure 9B:
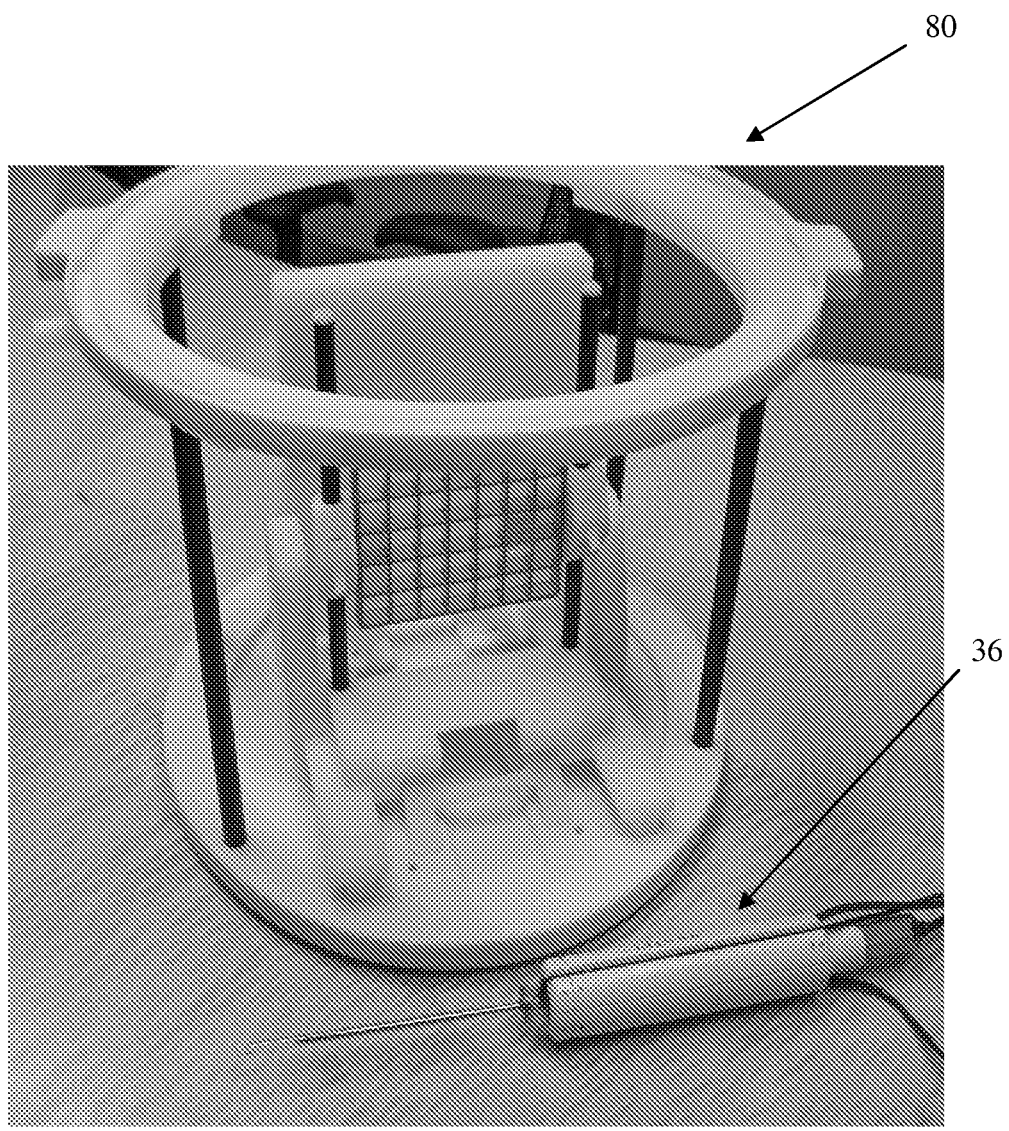
Figure 9C:
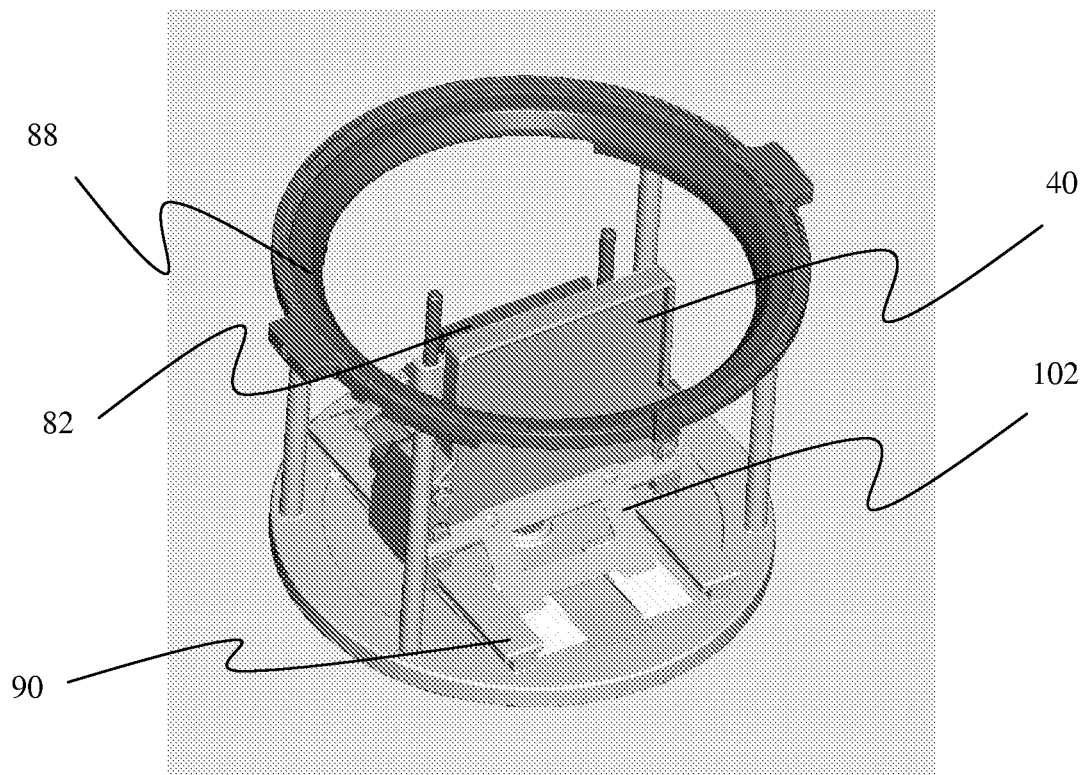
Figure 9D:
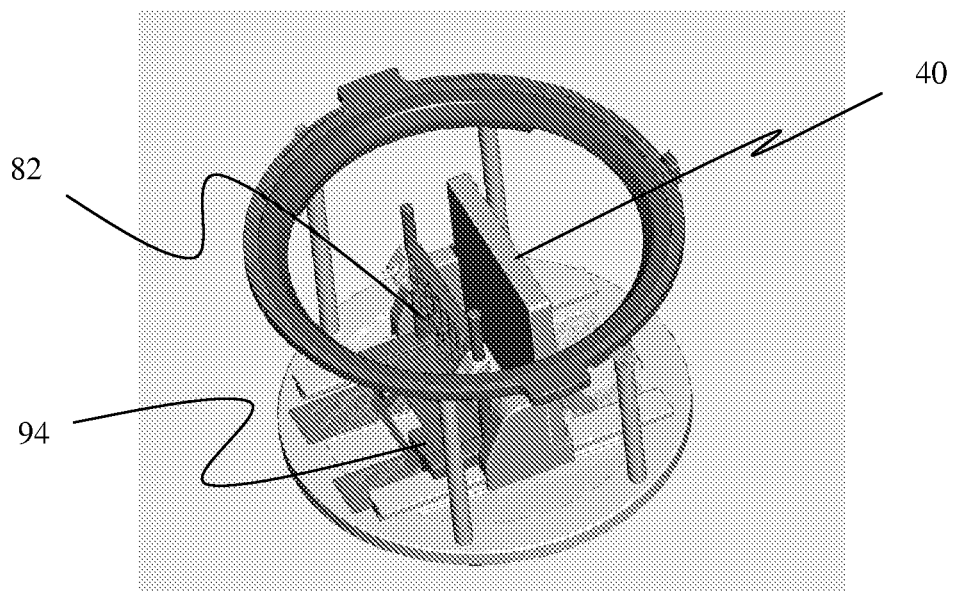

3. Scan with the biopsy needle 36 in place: To minimize the artifacts due to the metal biopsy gun and needle 36, which are large high-contrast objects, the projections can be taken along two separated segments of arcs (A and B) to avoid a full coverage of the biopsy gun and needle 36, as shown in FIG. 8. The missing data between the two arcs can be taken from the corresponding part in the scan in step 1. Thus the relative position of the needle 36 and the suspicious mass can be reconstructed with tolerable artifacts or errors. A low dose volume-of-interest (VOI) half scan method can be used for this step since a full circle scan can not be performed once the biopsy stage assembly is in place. It should be pointed out that the collimator could be opened to only expose the needle and the tumor 32, so the X-ray coverage at the breast 30 is less than ~(Δ+1) cm, where Δ is the maximum detected size of the tumor 32 by CBCT. The exposed area of the breast 30 is be greatly reduced by this approach.

An efficient half scan cone beam reconstruction algorithm has been developed and can be used in connection with embodiments described herein. The algorithm can be used for reconstructing tumor 32 and biopsy needle 36 with the half scan data in the preliminary phantom studies to determine the image quality and quantify the potential artifacts and errors. The data acquisition and reconstruction protocols can be evaluated in terms of the magnitude of artifacts, accuracy of the spatial relationship between tumor 32 and biopsy needle 36, data acquisition speed, required projection number for accurate imaging guidance, reconstruction speed and contrast to noise ratio for tumor images.

While imaging the relative position of the biopsy needle 36 and tumor 32 during the biopsy process, metal artifacts caused by the biopsy needle 36 should be considered. Since the biopsy needle 36 is made of metallic material, its attenuation coefficient is much higher than that of the surrounding breast tissue. This significant discontinuity in the projection data can cause streaking artifacts in the reconstruction images, which may block imaging of a nearby lesion.

Embodiments of the present disclosure are designed to correct for metal artifacts as follows: First, a derivative method is applied to localize the biopsy needle 36 in the projections. Secondly, to decrease the discontinuity caused by the metal, two methods can be tested. One is to decrease the projection value of the biopsy needle 36 proportionally according to its original value. The other one is to use spline interpolation based on the reduced sampling values at the biopsy needle location. Using both methods, part of the biopsy needle information can be kept in the projections and the position of the needle 36 can be reconstructed with less artifact. As a result, the relative position of biopsy needle 36 and target tumor 32 can be observed more clearly and measured more accurately from the reconstructed image in order to guide the biopsy process.

4. Biopsy and biopsy marker placement. In some embodiments, no scan is required in this step.

5. Post biopsy verification. This can be used to verify if the mass has been sampled properly. A half scan reconstruction can be sufficient for imaging, and the X-ray beam only needs to cover the needle 36 and the tumor 32 as in step 3.

6. Check the biopsy marker. The details for this scan are included in step 5.

Additional evaluations can be performed to verify and optimize the data acquisition and reconstruction protocols with phantom studies after the completion of the integration of the system.

Protocols for low-dose targeted volume scans and reconstruction can be used to accurately verify the position of the biopsy needle before sampling, with minimized required radiation dose and without requiring contrast injection. Embodiments of these protocols can include the following:

1. Computer-controlled collimation system to minimize the required glandular dose for targeted volume of interest scan: Optimize the collimator to provide flexible targeted collimation of imaging radiation to the region of interest minimizing, or reducing, X-ray dose to patient, achieving faster data acquisition and on-line reconstruction. In some embodiments, a custom collimator can be designed, to provide flexible targeted collimation of imaging radiation to the region of interest. Flexibility in positioning the lead shutters of the collimator to expose only the region of interest (tumor and biopsy needle) can aid in the reduction of total glandular dose to the breast 30, reduce scatter radiation resulting a better contrast to noise ratio, increase the speed of the scan (with a smaller detected area, the imaging system can read out at higher frame rates, for example 60 frames/second if needed), and reduce the time of reconstruction since the matrix size can be smaller. It is expected that the dose can be reduced by a factor of 5-15 of glandular dose for a whole breast depending on the coverage volume for the targeted scan. The size and location of the tumor 32 can be determined from the 3D reconstructed image from the first CBCT scan in the CBCT-GBx procedure. Those parameters can be fed into the control system of the motorized collimator for automatic optimized collimation. The relationships between collimation width (volume of interest [VOI]) and dose reduction as well as between the size of the VOI and scatter reduction, can be documented. With novel low dose targeted VOI scan protocols and reconstruction protocols, the total dose for the CBCT-GBx procedure can be less than that required for two whole breast scans (~800 mRad for average size normal breast).

2. Low dose targeted volume of interest scan protocols that facilitate near real-time CBCT image-guided localization and biopsy with minimized required radiation dose and without requiring contrast injection: With low dose targeted VOI scan, the speed of the scan can be increased. With a smaller detected area, the imaging system can read out at higher frame rates, for example 60 frames/second if needed. The time of data acquisition can be reduced to for half scan. A study indicates that the image lag and the measure lag, in some embodiments, is less than 3% if the frame rate is 30 frame/second, which will not affect the image quality of the reconstruction. Image lag can be measured for 60 frames/second rate and subtracted out prior to reconstruction if necessary.

3. VOI reconstruction protocols to achieve accurate and precise image-guided biopsy with near real time 3D reconstruction: Reconstruction protocols can be used to obtain projection image data from the CBCT-VOI scan. Truncation issues can be evaluated and addressed if they exist. Severe truncation artifacts for this VOI reconstruction are not expected since the filed of imaging can be collimated such that the whole width of the breast 30 that includes the targeted lesion is included in the acquired projection data. The reconstruction protocols can be optimized in terms of reconstruction speed.

Embodiments may provide that image guidance systems can be used to accurately provide for targeting by the clinician to determine lesion localization coordinates and parameters for biopsy, and similar, procedures. Such systems and protocols can include the following:

1. Image fusion algorithms to fuse the targeted volume of interest reconstruction images with the images of a whole breast 30 reconstructed previously for efficient and accurate on-line image-guidance of biopsy: Proper fusing of the VOI and full breast images can be achieved through registration of the same anatomical structure in both image data sets or with added fiducial markers, if desired. The fused image can be used by radiologists to plan the insert of biopsy needle 36. For this a simulated trajectory of the biopsy needle 36 can be fused with the CBCT 3D image of the breast/lesion and biopsy needle 36. This simulated trajectory of the biopsy needle 36 can be based on the coordinates and angle of the needle tip, as positioned by the image guided transport system, as well as the proposed insertion depth and stroke of the biopsy needle 36.

2. CBCT image guidance systems can be used to accurately provide for targeting by the clinician to determine lesion localization coordinates and parameters for biopsy and for the interface of CBCT image guidance system with biopsy support stage for accurate and efficient biopsy.

Embodiments of the present disclosure optimize 3D display protocols for near real-time image guidance for efficient localization and biopsy. In some embodiments, four scans are performed and the reconstructed images be displayed using client/server visualization software, for example, as follows:

1. The compressed breast 30 with tumor 32 can be scanned and the client/server can be used to locate the tumor 32 and the vessels in 3D space with respect to a (0, 0, 0) reference point. Since tumors and vessels have different linear attenuation coefficients compared to normal breast tissue, two different thresholds on the display using client/server can be used to find and automatically label them. Once they are labeled, their location and volume can be found by using the volume edit and statistics tools of client/server. These 3D coordinates can easily be obtained and transferred to the orbital 4-axis transport system. Since the large blood vessels and the tumors will be visible, the shortest path can be found from the breast surface to the tumor 32 without damaging relatively large blood vessels. The simulated proposed trajectory of the needle 36 to the sampling site can be fused with the actual 3D image to verify that the needle goes accurately go to the lesion and not damage any major vessels.

2. The biopsy needle tip can be moved by the orbital 4-axis transport system to the breast skin surface at the position indicated to give the best trajectory of the needle 36 to the lesion. An optical observation method can be performed to verify the position of the needle at the breast surface. This can be done visually by the technician, either directly, or using a remote camera system.

3. The biopsy needle 36 can be inserted into the breast 30 by the doctor so that it is just under the tumor 32. A second scan with low dose VOI acquisition and reconstruction mode can then be performed to verify the position of the needle 36 with respect to the tumor 32. The half scan method can be used since a full circle scan can not be performed once the biopsy stage assembly is in place. In order to quantify the distance of the needle 36 to the tumor 32, the measure tool of the client/server software can be used. After the needle-tumor spatial relation is confirmed by the clinician, the biopsy can then be performed.

4. A third scan with low dose VOI acquisition and reconstruction mode can be performed after the tumor 32 is sampled. In this scan, a cavity can be visible whose attenuation coefficient should be much lower than the surrounding tissue's attenuation coefficient. Again, a threshold can be set to visualize the cavity. Volume edit and statistics tools of the client/server software can be used again to evaluate the volume and location of the cavity.

5. A fourth scan with low dose VOI acquisition and reconstruction mode can be performed after a marker is placed in this cavity. Since this marker is made of a high contrast material, it can easily be seen and localized using Koning client/server's tools.

Table 3, below, provides embodiments of data acquisition protocols that can be implemented by the present disclosure:

TABLE 3

Data acquisition protocols

| SCAN | Step 1 | Step 3 | Step 4 | Step 5 |
|---|---|---|---|---|
| Scan type | full-scan | half-scan | half-scan | half-scan |
| # projections | 300 | 175 | 175 | 175 |
| FOV size | Full FOV | Small FOV | Small FOV | Small FOV |

For the CBCT system, the X-ray technique ranges can be 45-50 kVp, 50-100 mA and 5-8 ms. The X-ray can be filtered by a 2 mm thick aluminum plate to reduce the number of low energy photons that contribute to dose but contribute very little to the image. To make a trade-off of high image quality and low dose level, the entrance exposure to the breast 30 can be set to ~3 mR/projection for an average sized breast 30. Usually there will be 300 projections for a full scan and 175 projections for a half scan. It is expected that the process will result in ~400-500 mrad glandular dose to a whole breast 30 which is equal to or less than that of digital mammography for one breast scan assuming two views per breast are required. Also, the low dose VOI acquisition can deposit significantly less dose than the full scan of the entire breast 30 and propose as a goal a total 700 mRad glandular dose to the tissue in the region of interest for the whole procedure of one breast biopsy.

Biopsy Grid and Clamp System

FIGS. 9A-14B illustrate embodiments of a Biopsy Grid/Clamp system 80 that enables the Cone Beam CT-guided biopsy procedure (CBCT-Gx). In some embodiments, the system can implement vacuum-assisted percutaneous core breast biopsy systems. This system is designed for cone beam CT-guided biopsy of the breast and can provide detection and biopsy of many breast lesions that will only be seen with CBCT. This unique CBCT Biopsy Grid/Clamp device is compatible with an associated grid 82, needle block 84 and introducer set, which in some embodiments is commercially available.

In some embodiments, the Grid/Clamp system 80 includes the following features and/or advantages. It is easy to attach to patient tables 49 and to use for a standard biopsy procedure. In some embodiments, the system 80 has a low total weight (less than about 10 lbs). The system 80 is configured to firmly but comfortably hold the breast by compressing by feel in small (~1 mm) steps. The system 80 includes a quick release of compression and is simply constructed. The system is able to rotate 360 degrees around the breast before compression to obtain the shortest skin-to-lesion distance. The system comprises low x-ray attenuation materials that are in the imaging volume (to reduce x-ray intensity by <50% for most projection angles).

Embodiments of the system 80 provide an easily disassembled and system that is easily cleaned with standard clinical cleaning agents. The system 80 is compatible with a grids 82, needle block 84 and introducer set. The system allows technicians to get both hands between the back and front clamping plate to adjust the breast during compression. The system accommodates various breast lengths (chest wall-to-nipple), up to about 28 cm. The system 80 enables biopsy needle access up to and parallel to the chest wall.

The Grid/Clamp system 80 (FIG. 9A) and engineering prototype (FIG. 9B) were developed through several iterations based on feedback during research and development from manufacturing partners and mammography clinicians.

Figure 10A:
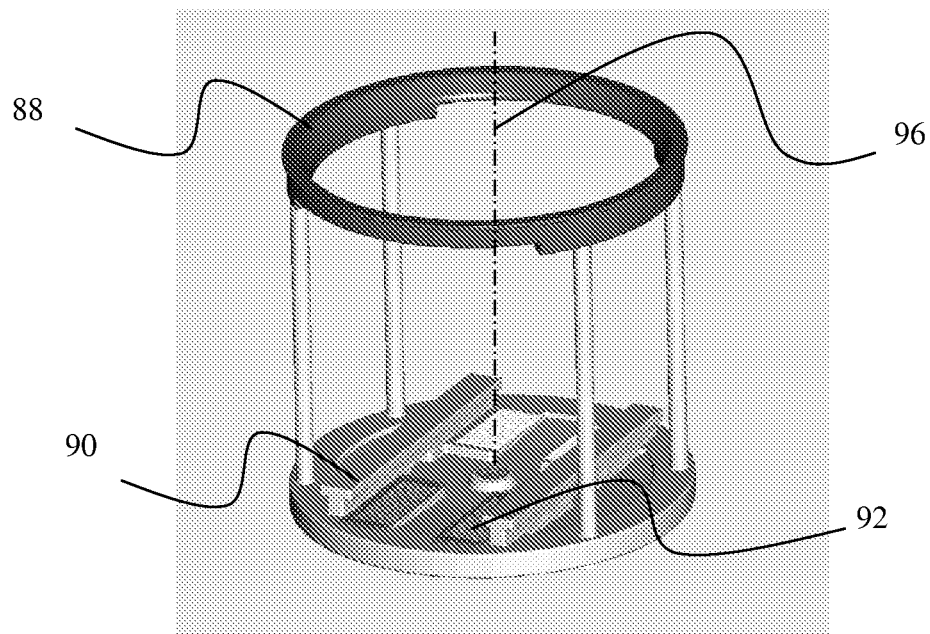
FIGS. 10A-10B illustrate embodiments of a frame subassembly for the clamp device.
Figure 10B:
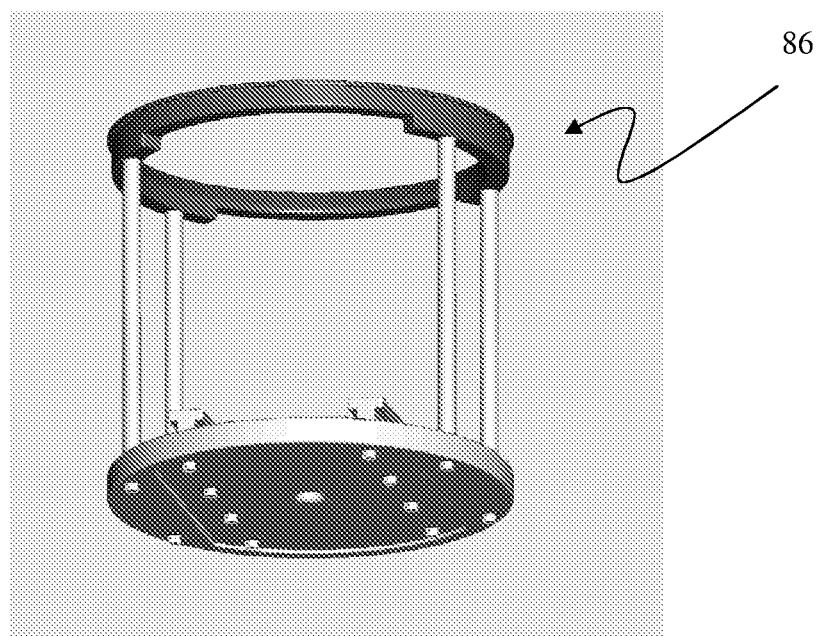

FIGS. 9A-9D, and 10A-10B provide views of the Grid/Clamp system 80 and an associated frame sub-assembly 86. Shown in the figures is the upper ring 88 and lower plate rigidly connected together by ~4 carbon-fiber rods. This provides a very stable frame 86 for the grid/clamp assembly. These also show the rail mount 90 on the base for the grid/clamp structures. This assembly is well-sealed to easily clean any bodily fluids after a biopsy procedure. A central clear acrylic window allows the laser alignment light to indicate the position of the axis of rotation on the breast for centering purposes. The base also shows the stepped plates 92 which will allow near continuous motion of the compression plate 40 and grid holder 94 with position locking. Also depicted in FIG. 10A is a central axis 96 of the Grid/Clamp system 80 that preferably coincides with the axis about which the system 28 is capable of rotating.

Figure 11A:
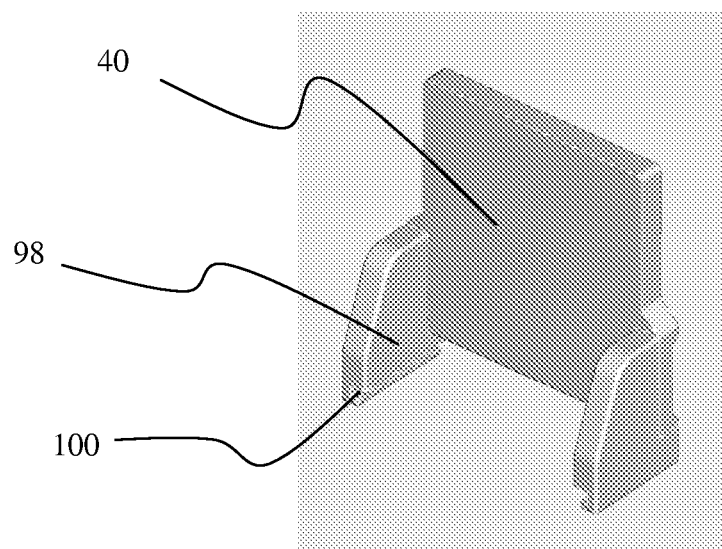
FIGS. 11A-11B illustrate embodiments of a back compression plate for the clamp device.
Figure 11B:
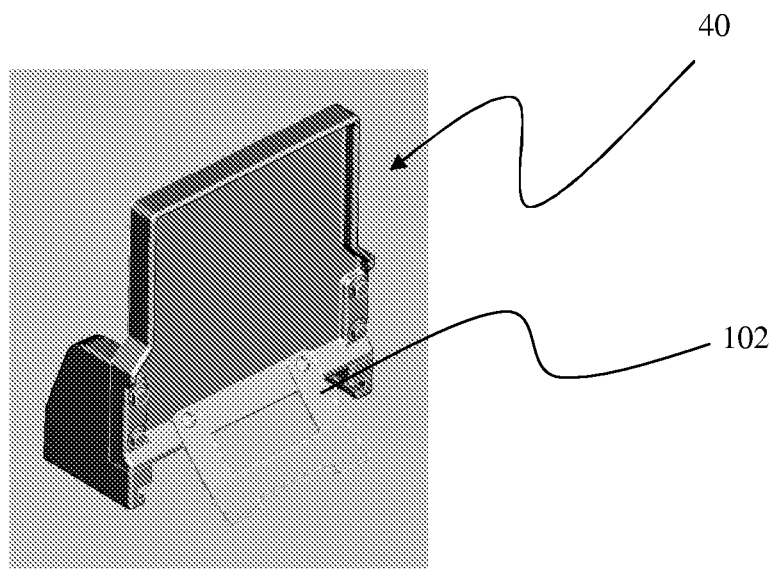

FIGS. 11A-11B depict views of the back compression plate 40 show the mounting brackets 98 with rail slot 100 and ratcheting flap 102 that provide near continuous motion with position locking against the stepped plates 92. The ratcheting flap 102 engages the stepped plates 92 for locking the corresponding compression plate 40 or grid holder 94 into place. This assembly is well-sealed to easily clean off any bodily fluids after a biopsy procedure.

Figure 12A:
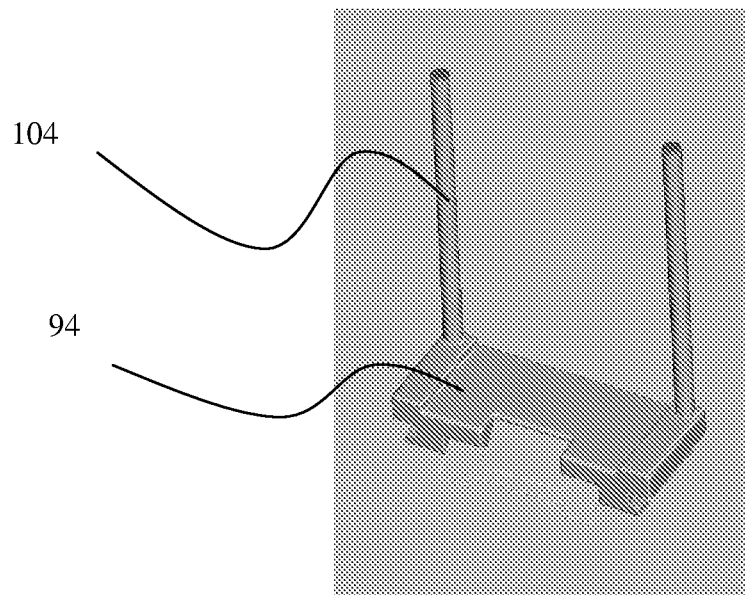
FIGS. 12A-12B illustrate embodiments of a grid holder.
Figure 12B:
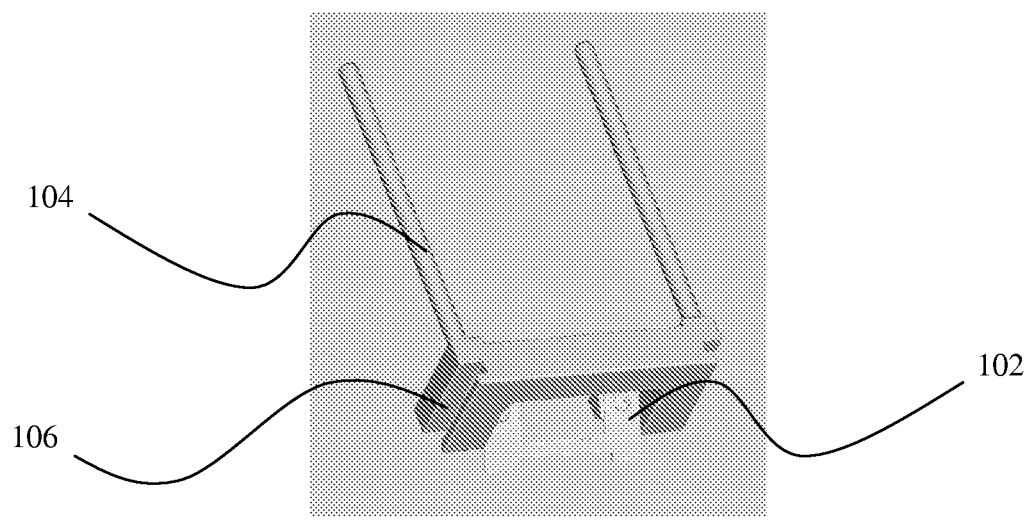

FIGS. 12A-12B illustrate views of the grid holder 94 show the grid rails 104, the mounting rail slots 106, and ratcheting flap 102 that provide near continuous motion with position locking. This part holds the commercially available grid 82 and allows vertical positioning of the grid 82 to the lesion location in the breast 30. This assembly is well-sealed to easily clean off any bodily fluids after a biopsy procedure.

Figure 13A:
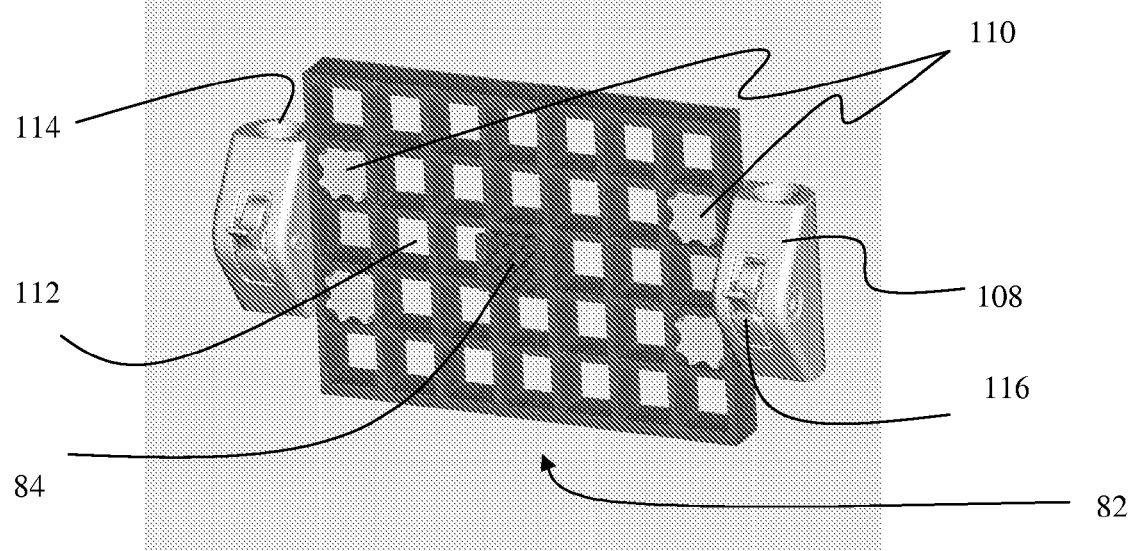
FIGS. 13A-13B illustrate embodiments of a grid clamp.
Figure 13B:
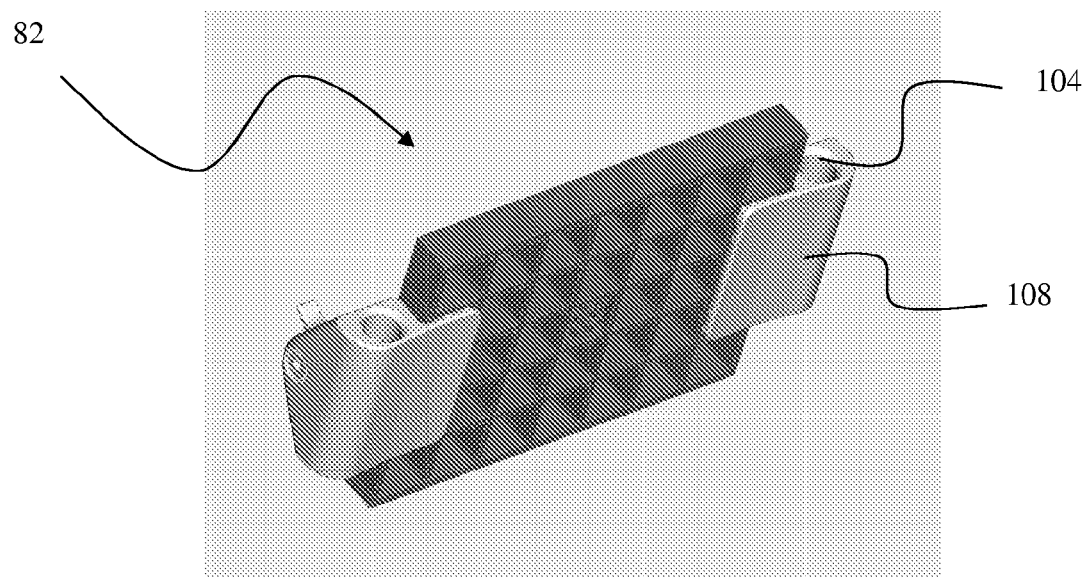

FIGS. 13A-13B depict views of the grid showing the mounting grid clamps 108 that hold the commercially available grid 82 and needle block 84. They provide near continuous vertical motion of the grid to the lesion location in the breast with position locking. These grid clamps are coupled to the grid by friction fit inserts 110 that fit within apertures 112 of the grid and are easily removed from the grid and are well-sealed to easily clean off any bodily fluids after a biopsy procedure. The clamps 108 comprise an opening 114, through which the grid rails 104 of the grid holder 94 are received. Movement between the grid 82 and the grid holder 94 along the grid rails 94 is permitted or limited by actuation of grid clamp switches 116 that can be used to lock the grid 82 into position.

FIG. 13B depict the grid/clamp subassembly 80 showing embodiments of the mounting grid clamps 108 that hold the commercially available grid and needle block. They provide near continuous vertical motion of the grid 82 to the lesion location in the breast with position locking. These grid clamps 108 are easily removed from the grid 82 and are well-sealed to easily clean off any bodily fluids after a biopsy procedure.

Figure 14A:
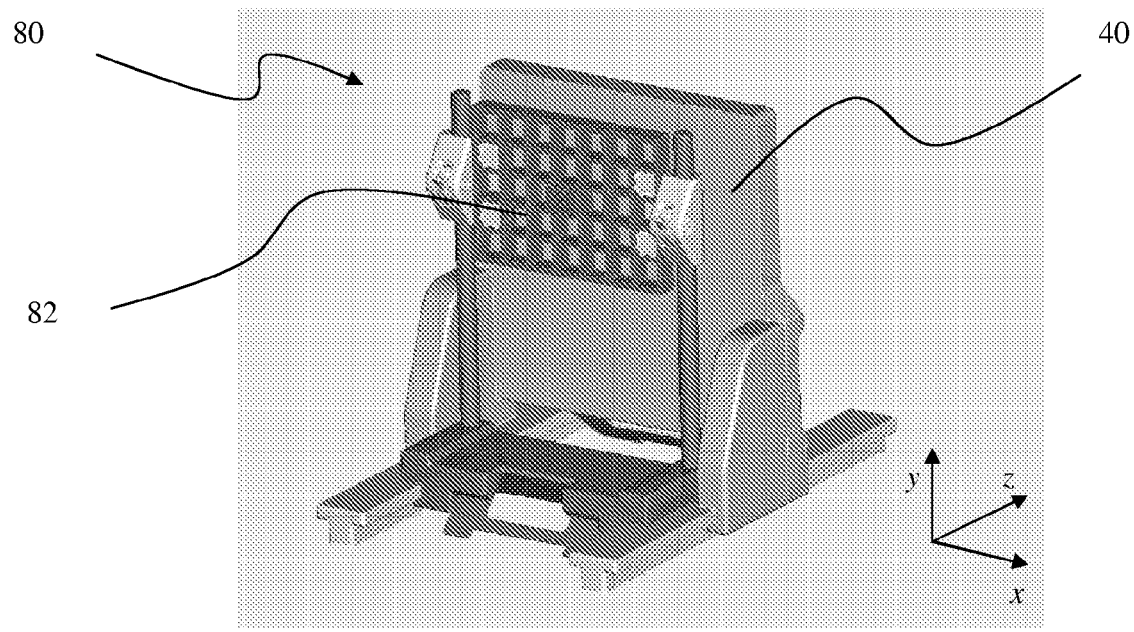
FIGS. 14A-14B illustrate embodiments of a grid clamp and a back compression plate.
Figure 14B:
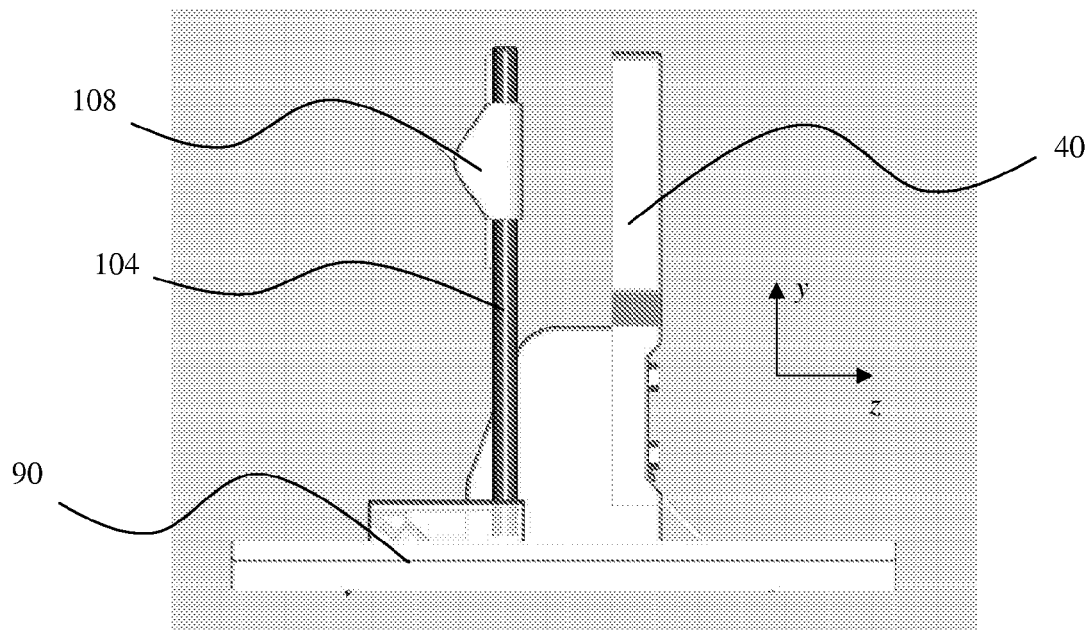
Figure 14C:
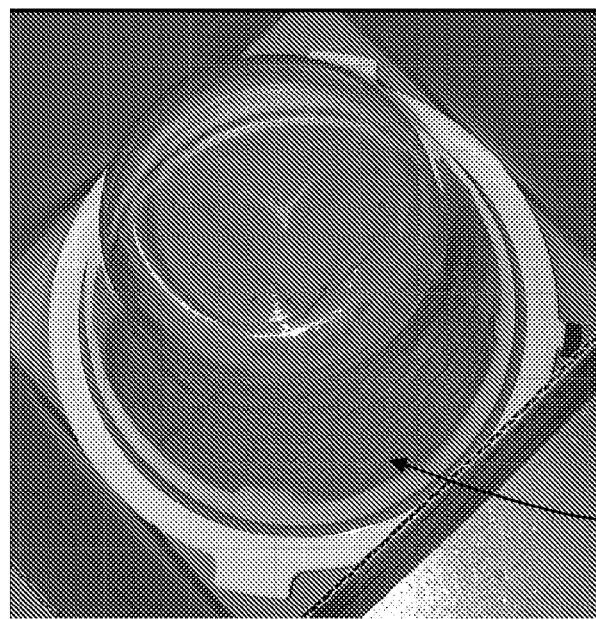
FIGS. 14C-14D depict embodiments of a safety cover.
Figure 14D:
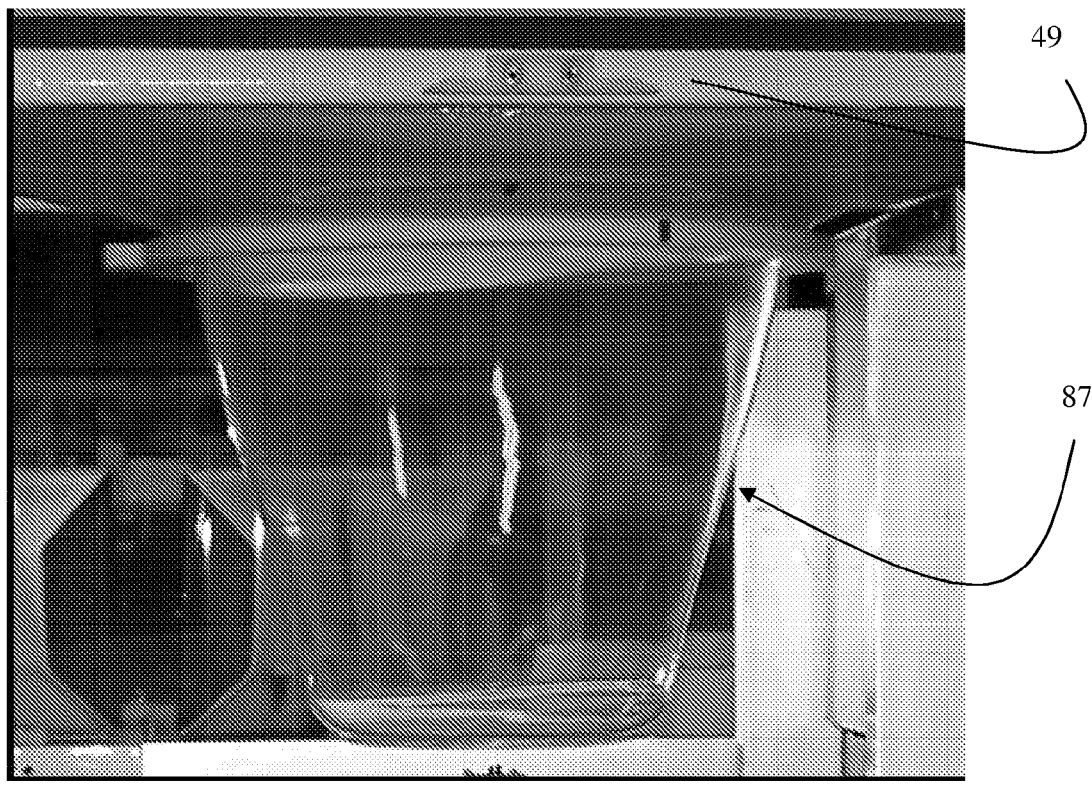

FIGS. 14A-14B depict views of the full grid/clamp assembly 80 showing the full assembly except for the frame subassembly 86. The assembly 80 can be coupled to the table 49 by a flange that provides 360 degrees of angular adjustment to position the grid on the breast 30 for the minimum skin-to-lesion distance with angular position locking.

In some embodiments, the system 28 includes a safety cover 87 (FIGS. 14C-14D) that is positioned underneath the patient table 49 at the opening where the breast is placed. The safety cover prevents, or limits, access to the rotating gantry by the patient positioned on the table and prevents, or limits, items from inadvertently falling into the hole and onto the rotating gantry. In some embodiments, the safety cover 87 comprises a cylinder made of low or very low x-ray attenuation material (e.g., polycarbonate), is optically transparent, is easily attached and removed, and/or has an interlock with the patient table 49 that prevents, or limits, motion or x-ray emission if the safety cover 87 is not in place. In some embodiments, the safety cover 87 is about 30 cm in diameter and about 30 cm long, and in certain embodiments, the safety cover's attenuation reduces the intensity of the x-ray beam by less than about 10%.

In some embodiments, a procedure for using the Grid/Clamp system 80 can include the following: based on a previously obtained image of the lesion 32 within the breast 30, the breast 30 is positioned in the biopsy grid/clamp device/system 80 to cover of the area of concern and suitable skin to lesion distance. A CBCT study, comprising data that can be used to produce an image, of the breast is performed. A 3D rendering of the breast is created and indicates the exact position of the suspicious mass in the breast, as determined in the 3D imaging space. Using 3D imaging, the physician observes and marks the location of the suspect target in the 3D coordinate system. From this pre-biopsy scan, the optimal grid location and needle-guide hole is determined that gives optimal trajectories of the biopsy needle 36 to the lesion while avoiding major vessels (seen with CBCT without contrast). Skin-to-lesion depth is also determined from the CBCT 3D imaging.

The patient's skin is prepped using an aseptic technique at the appropriate block of the grid. The skin and deep to the lesion is anesthetized. The needle guide is inserted into the compression grid at the appropriate grid location. An introducer stylet is inserted and hubbed to the introducer sheath; a "depth stop" on the introducer sheath is placed in the appropriate location based on the skin-to-lesion depth determined from the CBCT 3D imaging.

The stylet is removed from the introducer sheath leaving the introducer sheath in place. The localizing obturator is inserted into the introducer sheath, and the breast is imaged to confirm accuracy of position. The localizing obturator is removed and the biopsy needle is inserted to biopsy the area of interest. Once the biopsy is completed, the biopsy device is removed (leaving the introducer sheath in place). Post-biopsy imaging is completed to confirm the biopsy of suspect area.

A radiopaque marker can be placed at the biopsy site through the introducer sheath for future intervention or treatment localization and the location verified with CBCT imaging. After the marker placement and confirmation scan, the introducer sheath is removed. The breast is then removed from compression, pressure is applied to the biopsy area to stop bleeding, and a sterile gauze bandage will be applied for pressure as well as ice to minimize bruising.

Exemplary Procedure for Cone Beam CT Localization and Guidance

In some embodiments, one or more of the following steps can be used in to obtain data sets for 3D visualization of the breast 30, for the purpose of: visualizing and targeting the lesion of interest, verifying the position of the biopsy needle 36, documenting lesion sampling/complete removal, and verifying clip placement.

Some embodiments provide a method that allows the clinician to verify actual needle placement using a half-scan method. In some embodiments, the table is placed at the Scan Position (minimum height) with the gantry doors in the closed position. The patient accesses the table, from either end (as determined by the diagnostic scan for ease of team access) and lays prone, with the breast 30 of interest pendant through the table aperture. The table is elevated to a convenient height for the biopsy team and the gantry doors are opened for access. The technologist attaches the CBCT-LG access window/compression assembly. Based on imaging or a diagnostic scan, the technologist can rotate the assembly to the appropriate theta angle. The technologist optimizes breast position in the access window and compression is applied.

The technologist collimates to the volume of interest to minimize X-ray exposure to the breast 30, reduce scatter and reduce image reconstruction time and the gantry doors are closed for image acquisition. Image acquisition in the full-scan mode: 3D image is rendered and reviewed. Based on the 3D rendering and slice data, the radiologist can target the lesion of interest and determine the preferred needle trajectory. The $P_{entry}(P_x, P_y, P_z, \Delta\theta')$ coordinates are calculated by the computer. Pre-fire depth (back-off) and stroke margin are calculated.

The gantry doors are opened for access and the $P_{entry}(P_x, P_y, P_z, \Delta\theta')$ coordinates are transferred and verified. The orbital 4-axis transport system with biopsy instrument/needle combination and appropriate needle guide are attached to the system. The skin is prepped and the biopsy device/needle is driven to match the lesion's x, y, z and theta coordinates. The skin and deep tissue are anesthetized and a skin incision is made. The depth stop is set for the Z coordinate and the needle 36 is manually advanced into the patient's breast to the appropriate pre-fire depth; the gantry doors are closed.

Low-dose VOI image acquisition in the half-scan mode is accomplished: 3D image and slice data is rendered & reviewed for needle placement accuracy. The gantry doors are open. Presuming accurate needle placement, the biopsy instrument is fired and the lesion is sampled. The needle is removed from the breast 30 and the instrument is removed from the support.

Post biopsy imaging is acquired to assure lesion removal. Tissue marker clip placement is accomplished through a posterior and anterior guide. The support is re-driven to the lesion's x, y, z and theta coordinates and the depth stop set for appropriate Z depth. The clip deployment tool is placed through the posterior and then anterior needle guides to the appropriate depth and the clip is dropped and post-clip placement imaging is acquired. Another low-dose VOI image acquisition in the half-scan mode may be performed for marker placement verification. In some embodiments, an alternative obturator method can also be used with full-scan imaging.

In some embodiments, the systems and methods can provide that the patient drop the shoulder into imaging field for better axilla coverage, provide support of shoulder to relieve pressure on neck, provide more support at the belly to keep it out of the imaging field and narrower the width of the opening in the table to keep non-imaged breast from falling into the imaging field.

CBCT-GBx System Using Compressible Phantoms with Pseudo Tumors Calcifications Glandular Structure and Vessel Inserts To simulate the whole biopsy procedure, and compare the results obtained by CBCT with stereotactic biopsy (the current standard of care) a set of biopsy phantoms can be used to perform the identical studies on CBCT as well as with stereotactic biopsy. Current stereotactic biopsy techniques can produce satisfactory biopsy sampling for suspicious masses that are 5-15 mm in diameter as well as for calcifications. However, these techniques are limited by breast thickness, requiring the need for high kVp in thick instances, which reduces image contrast to resolve lesions and overlapping structures. In addition, stereotactic imaging is limited in visualizing small (<5 mm) tumors. Since CBCT provide sensitivity effective to locate tumors as small as 2 mm, and calcifications as small as 0.2 mm, a more accurate and precise localization and guidance system can be useful when used with CBCT. Phantom studies can verify that the CBCT image-guided localization and guidance system has at least an equivalent success rate to stereotactic localization in biopsying tumors and calcifications or better successful rate for tumors under 10 mm.

In some embodiments, phantoms can be provided that are non-uniform in make-up, as opposed to tissue equivalent phantoms, and 9 phantoms can consist of background material of 50/50 adipose/glandular structure. Simulated glandular structures can randomly infiltrate throughout the phantom volume to serve as overlapping structure similar to that in real breasts. Simulated major vessels can also be distributed within the phantoms to test the vessel avoidance capability of both image-guided biopsy systems. There can be for example 3 sizes of phantoms, small, medium and large, and each size can have sets of masses: 10-15 mm, 5-10 mm, and 2-5 mm. Each phantom can be designed to include 10 tumors of a given tumor range so that one phantom can be biopsied 5 times under both CBCT-guided biopsy and stereotactic-guided biopsy. In addition, they can contain 10 collections of calcifications imitating clusters of 3-10 mm. In addition, 3 medium size phantoms, each with a set of 10 tumors (one each per tumor range) and calcifications and consisting of background material of 25/75 adipose/glandular structure, to simulate a dense breast, can be provided.

Since calcification distribution may be linear across planes, the phantoms can also include representative lesions, with distributions over at least 2 cm interval. Individual calcifications can range from 0.16-0.54 mm (as in the ACR mammography phantom). In some embodiments, the method comprises performing 5 biopsy tests for each size range of tumors and calcifications, to quantify the accuracy and precision of the CBCT image-guided localization and guidance system for biopsy. An additional 5 tests for each size range of tumors and calcifications can be performed with a stereotactic biopsy system. Based on previous imaging studies to quantify reconstructed volume accuracy and the current precision of commercial encoder feedback transport systems, it is expected that embodiments of a CBCT image-guided orbital 4-axis transport system for biopsy can provide precision within +/−0.5 mm.

For the phantom studies, a CBCT scan can be used to verify accurate positioning. Once correct targeting is confirmed, tissue sampling can be performed using a vacuum-assisted breast biopsy device through the coaxial sheath. In some cases, sampling can be performed in the direction of the lesion. When tissue sampling is complete, the probe can be retracted and a site marker placed through the coaxial sheath. A final CBCT image of the biopsied region can be performed to verify the location of the sampling defect and of the site marker. In an exemplary method, the steps can comprise: (a) scan the compressed breast 30 with the breast access window/compression assembly in position; (b) optically verify that the biopsy needle is at the proper place at the breast surface; (c) scan with the biopsy needle 36 in place; and (d) perform biopsy and biopsy marker placement; (e) perform post biopsy verification and check the biopsy marker.

Regulatory requirements state that facilities performing diagnostic x-ray procedures (radiology, fluoroscopy, x-ray bone densitometry or computed tomography) develop and continually implement a Quality Assurance (QA) program. The regulations apply to equipment used on humans in hospital, medical, pediatric, chiropractic, industrial, school, and government facilities. A QA program, which includes quality control (QC) tests, helps ensure that high quality diagnostic images are consistently produced while minimizing radiation exposure. This program will enable the facility to recognize when parameters are out of limits, resulting in poor quality images and increasing the risk of radiation exposure to patients. QC tests will be performed with a QC Phantom, as discussed above, especially designed for cone beam breast CT. Simply performing the quality control tests is not sufficient. When quality control test results exceed established operating parameters, appropriate corrective action must be taken immediately and documented. This QC phantom can also be used as a performance phantom for simple visual daily checks by clinical technologists to ensure proper operation of the Koning Breast CT system before scanning patients (low contrast resolution, spatial resolution, and uniformity/artifacts).

Figure 15A:
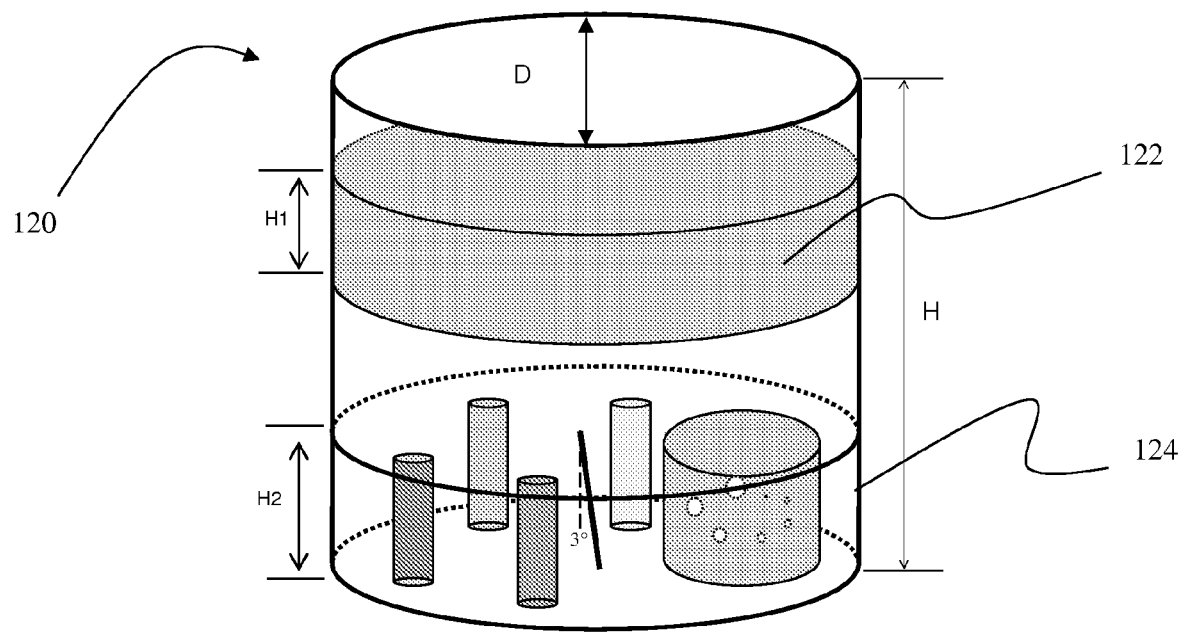
FIGS. 15A-15C illustrate embodiments of CT quality control phantom.
Figure 15B:
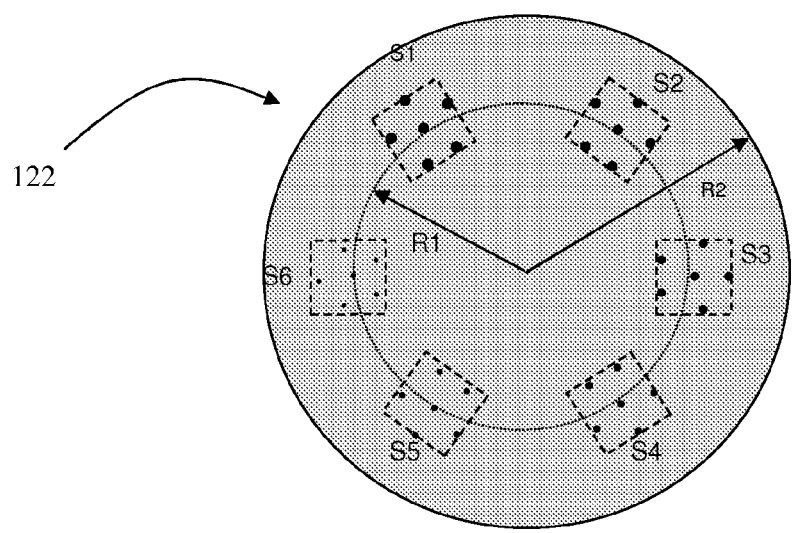
Figure 15C:
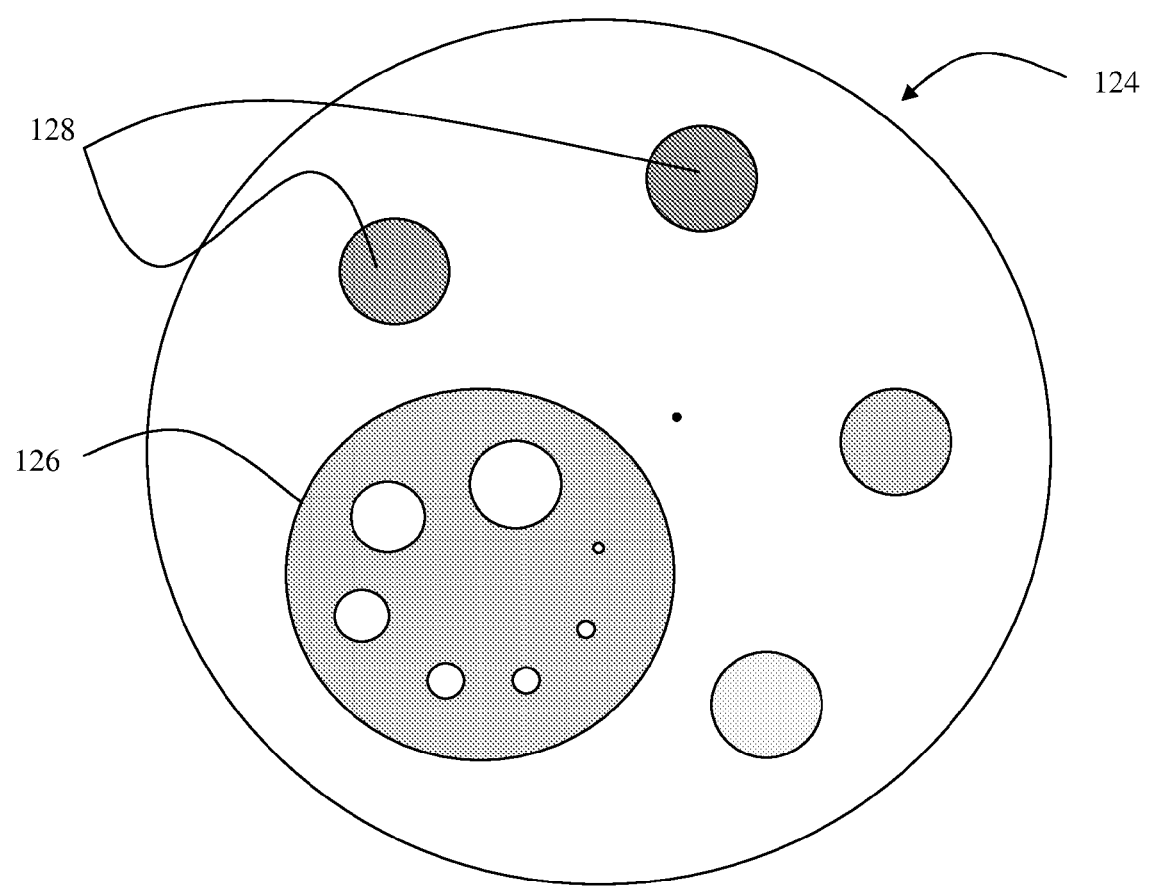

Illustrated in FIGS. 15A-15C are embodiments of QC phantoms 120 that can be used for testing purposes. In some embodiments, the phantom 120 includes insert 1 122 and insert 2 124. The image quality parameters addressed by this QC/Performance phantom include uniformity (clear water region), CT # accuracy (clear water region), noise (clear water region), high contrast spatial resolution (insert 1 122), low contrast resolution (insert 2 124, section 1), CT # linearity (insert 2 124, section 2), and Modulation Transfer Function (MTF) (insert 2, section 3).

The design of the QA phantom is illustrated as in FIG. 15A. In some embodiments, the phantom 120 can have a diameter D of about 13 cm (and range between about 10 cm and 16 cm) and a height H of about 10 cm. In some embodiments, insert 1 122 can have a height H1 of about 2 cm, and insert 2 124 can have a height H2 of about 3 cm. In some embodiments, the phantom 120 can be larger, with greater dimensions, and the phantom can be small, with small dimensions. The phantom 120 perferably includes one cylindrical container and two inserts. It will be used routinely for the image quality assurance program. The phantom 120 is preferably filled with water to measure the water attenuation coefficient, CT# accuracy, image uniformity, and noise.

Insert 1, depicted in FIG. 15B, is a high-contrast spatial resolution insert. It is made of BR12 (or equivalent), which is equivalent to 50%/50% adipose/glandular tissue, and contains about six calcification speck patterns ("S1"-"S6") simulated by calcium carbonate grains of about 165-375 microns in diameter. The speck pattern size is about 13.5×13.5 mm. These calcification speck patterns are spaced along about a 3.0 cm radius circle R1 at the same slice plane in the insert while R2 represents the radius of the insert.

Insert 2 124 contains multiple sections, including a low-contrast resolution section 126, which is made of BR12 (or equivalent) and contains several spherical "tumors" of different sizes. The tumors are made of a special material that gives about 20 HU contrast against the background. The diameters of the tumors range from about 2 mm to about 10 mm. Also included in insert 2 124 is a CT number-linearity section, which consists of several rods 128 (~1.2 cm diameter) made of different materials to cover ~+/−1000 HU. They have CT# equivalence to tissues such as adipose, breast, muscle, as well as iodine at ~200 mgI/cc. Insert 2 124 also preferably includes a MTF measurement section, which consists of a ~36 micron tungsten wire which is vertically tilted by ~30 to achieve a smooth MTF curve.

For lesion visualization, masses can be measured and compared to actual measurements. Differences between stereotactic and CBCT measurements can be tested with a paired comparisons t-test. Calcifications can be counted and clusters and distributions of calcifications measured. Differences between stereotactic and CBCT measurements of the number of calcifications can be statistically evaluated using a paired comparisons t-test.

For Calcium retrieval, X-ray imaging can be performed and calcium retrieval documented as a binary success/failure variable. The difference in success rate between stereotactic and KCBT localization can be tested using a McNemar test.

For mass retrieval, using software display tools, the mass "lesions" can be false-colored differently from the background structures. The amount of lesion removed can, and removal documented as a binary success/failure variable. The difference in success rate between stereotactic and KCBT localization can be tested using a McNemar test. Photographs of the specimens can be taken to document lesion removal For post-biopsy imaging of the phantom breast, evidence of lesion removal can be documented.

In all tests, the success/failure variable can be correlated with lesion size using logistic or linear regression as appropriate. It is anticipated that 1) for the tumors with the size ≥about 10 mm, CBCT-GBx can be at least equivalent to or better than the stereotactic biopsy system in terms of accuracy and precision of localization, targeting and biopsy, 2) for the tumors with the size in about 5-10 mm, CBCT-GBx, can be significantly better than the stereotactic biopsy system in terms of accuracy and precision of localization, targeting and biopsy, and 3) for the tumors with the size between about 2-5 mm, CBCT-GBx, can still have clinically acceptable accuracy and precision of localization, targeting and biopsy while the stereotactic biopsy system is unlikely to be able to visualize the tumors with high confidence.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A method, for detection, diagnosis, or treatment of a lesion in a patient's breast using a cone beam computed tomography (CT) guided biopsy system, the method comprising:
   providing a patient table, configured to position a patient for a biopsy procedure;
   providing a cone beam CT module, configured to output a cone beam CT image of at least a portion of the patient's breast;
   providing a compression module configured (i) to stabilize the breast during imaging and biopsy and (ii) to revolve around the breast;
   determining, from a diagnostic scan of the breast, an angular position of the compression module based on skin-to-lesion distance;
   orienting the compression module based on the angular position and compressing the breast with the compression module;
   outputting from the cone beam CT module a 3D reconstruction of at least a portion of the breast that includes a lesion;
   determining a path through which to guide a biopsy needle to the lesion, based on the 3D reconstruction;
   providing a multi-axis transport module, configured to move the biopsy needle along the path to the lesion;
   moving the biopsy needle from a location outside the patient's body to the lesion;
   taking projections (a) along two separated arcs, together forming less than a complete revolution about the breast and avoiding full coverage of the biopsy needle and corresponding biopsy gun, and (b) while collimating to expose only the biopsy needle and a portion of the breast including the lesion in an area not greater than 1 cm plus a maximum detected size of the lesion;
   reconstructing an image from the projections taken along the two arcs, and a part of the diagnostic scan, the part corresponding to data missing between the two arcs; and
   correcting for metal artifacts by (I) applying a derivative method to localize the biopsy needle in the projections, and (II) decreasing discontinuity by (A) decreasing a projection value of the biopsy needle proportionally according to its original value, and (B) using spline interpolation based on reduced sampling values at a location of the biopsy needle.

2. The method of claim 1, further comprising removing at least a portion of the lesion with the biopsy needle.

3. The method of claim 1, further comprising determining a volume of interest, wherein the volume of interest comprises a portion of the breast that includes the lesion.

4. The method of claim 1, further comprising orienting the compression module so the angular position permits the path, for the biopsy needle, to have a minimal skin-to-lesion distance.

5. The method of claim 1, further comprising marking an entry point with a light projected onto the surface of the patient's body.

6. The method of claim 1, further comprising determining, in the 3D reconstruction, a position of at least one of the biopsy needle, the lesion, a surface of the patient's body, a region of entry into the patient for the biopsy needle, a vessel, and the path between the region of entry and the lesion.

7. The method of claim 1, wherein determining the path comprises avoiding a physical structure in the breast.

8. The method of claim 1, wherein determining the path comprises avoiding penetration of the chest wall by the biopsy needle.

9. The method of claim 1, further comprising placing a fiducial marker at a site marking a position indicative of a location of the lesion.

10. The method of claim 1, wherein the determining the path comprises determining a distance between an area on a surface of the patient's body and the target of interest.

11. The method of claim 10, wherein the distance comprises a minimum distance among a set of distances from a corresponding set of points of entry on the patient's body, and the target of interest.

12. A method, for performing a cone beam CT guided breast biopsy, comprising:
providing a cone beam CT module configured to guide a biopsy needle to a site of a lesion located in a patient's breast, based on cone beam CT images provided by the cone beam CT module;
providing a compression module configured (i) to stabilize the breast during imaging and biopsy and (ii) to revolve around the breast;
imaging the breast to detect a lesion;
determining a volume of interest, wherein the volume of interest includes a portion of the breast in which a lesion is located;
determining, from the imaging of the breast, an angular position of the compression module based on skin-to-lesion distance;
orienting the compression module based on the angular position and compressing the breast with the compression module;
positioning a biopsy needle in a location effective to sample the lesion, based on guidance provided by the cone beam CT module;
collimating the cone beam CT to limit a field of view in an image of the volume of interest during sampling of the lesion;
determining a needle trajectory, comprising coordinates $P_{entry}(P_x, P_y, P_z, \Delta\theta')$, wherein the trajectory begins at Pentry, and ends substantially at the lesion;
positioning the biopsy needle substantially at the lesion, according to the coordinates $P_{entry}(P_x, P_y, P_z, \Delta\theta')$;
scanning the volume of interest to confirm needle position prior to sampling the lesion, the scanning comprising taking projections (a) along two separated arcs, together forming less than a complete revolution about the breast and avoiding full coverage of the biopsy needle and corresponding biopsy gun, and (b) while collimating to expose only the biopsy needle and a portion of the breast including the lesion in an area not greater than 1 cm plus a maximum detected size of the lesion;
reconstructing an image from the projections taken along the two arcs, and a part of a prior scan, the part corresponding to data missing between the two arcs;
correcting for metal artifacts by (I) applying a derivative method to localize the biopsy needle in the projections, and (II) decreasing discontinuity by (A) decreasing a projection value of the biopsy needle proportionally according to its original value, and (B) using spline interpolation based on reduced sampling values at the location of the biopsy needle;
sampling the lesion; and
removing the biopsy needle from the patient.

13. A method, for detection, diagnosis, or treatment of a lesion in a patient's breast using a cone beam computed tomography (CT) guided biopsy system, the method comprising:
determining, from a scan of the breast and based on skin-to-lesion distance, an angular position of a compression module configured (i) to stabilize the breast during imaging and biopsy and (ii) to revolve around the breast;
outputting the angular position;
receiving, from a cone beam CT module, an input indicative of a 3D reconstruction of cone beam CT data indicative of a lesion in the patient's breast;
based on the input, determining a path through which to guide a biopsy needle to the lesion; and
outputting machine readable instructions to a multi-axis controller of the biopsy needle, resulting in movement of the biopsy needle along the path to the lesion;
taking projections (a) along two separated arcs, together forming less than a complete revolution about the breast and avoiding full coverage of the biopsy needle and corresponding biopsy gun, and (b) while collimating to expose only the biopsy needle and a portion of the breast including the lesion in an area not greater than 1 cm plus a maximum detected size of the lesion;
reconstructing an image from the projections taken along the two arcs, and a part of the scan, the part corresponding to data missing between the two arcs; and
correcting for metal artifacts by (I) applying a derivative method to localize the biopsy needle in the projections, and (II) decreasing discontinuity by (A) decreasing a projection value of the biopsy needle proportionally according to its original value, and (B) using spline interpolation based on reduced sampling values at a location of the biopsy needle.

14. The method of claim 13, wherein the determining the path comprises avoiding a physical structure in the breast.

15. The method of claim 13, wherein the determining the path comprises determining a distance between an area on a surface of the patient's body and the lesion.

16. The method of claim 15, wherein the distance comprises a minimum distance among a set of points of entry on the patient's body and the lesion.

* * * * *